(12) United States Patent
Bucher et al.

(10) Patent No.: US 10,094,367 B2
(45) Date of Patent: Oct. 9, 2018

(54) METHOD AND SYSTEM FOR GENERATING MECHANICAL WAVES

(71) Applicant: Technion Research & Development Foundation Limited, Haifa (IL)

(72) Inventors: Izhak Bucher, Haifa (IL); Eyal Setter, Ramat-Yishai (IL)

(73) Assignee: Technion Research & Development Foundation Limited, Haifa (IL)

( * ) Notice: Subject to any disclaimer, the term of this patent is extended or adjusted under 35 U.S.C. 154(b) by 1085 days.

(21) Appl. No.: 13/772,506

(22) Filed: Feb. 21, 2013

(65) Prior Publication Data

US 2013/0216400 A1 Aug. 22, 2013

Related U.S. Application Data

(60) Provisional application No. 61/601,629, filed on Feb. 22, 2012.

(51) Int. Cl.
*A61B 1/00* (2006.01)
*A61B 1/01* (2006.01)
(Continued)

(52) U.S. Cl.
CPC .......... *F04B 43/12* (2013.01); *A61B 1/00156* (2013.01); *A61B 1/01* (2013.01);
(Continued)

(58) Field of Classification Search
CPC ............ A61B 1/00151; A61B 1/00156; A61B 1/0016; A61B 1/01; A61B 1/041; A61B 1/31; A61B 34/30; A61B 34/32; A61B 34/35; A61B 34/37; A61M 25/01; A61M 25/0105; A61M 25/0116; A61M 25/0122; F04B 7/0057; F04B 7/0061; F04B 7/0065; F04B 7/0069; F04B 1/0413; F04B 1/0417; F04B 1/0426; F04B 1/043; F04B 1/0472; F04B 1/0531; F04B 9/042; F04B 27/0414; F04B 27/0418; F04B 27/0428; F04B 27/0432; F04B 27/047; F04B 27/0472;
(Continued)

(56) References Cited

U.S. PATENT DOCUMENTS 3,066,637 A 12/1962 Akutowicz
3,154,043 A 10/1964 Momsen, Jr.
(Continued)

OTHER PUBLICATIONS

Chan et al. "Building a Better Snail: Lubrication and Adhesive Locomotion", Physics of Fluids, 17: 113101-1-113101-10, 2005.
(Continued)

*Primary Examiner* — Ryan Henderson

(57) ABSTRACT

A system for generating a mechanical wave is disclosed. The system comprises a camshaft having plurality of rotatable cams, serially mounted on a shaft along an axis of an elastic tubular shell to form a varying phase angle along the shaft. The system further comprises a plurality of cam followers arranged circumferentially about each cam, such that a rotary motion of the cams generates a linear motion of the cam followers to radially bias in internal wall the shell. The variation of the phase angle is selected to generate a three-dimensional traveling wave along the shell.

26 Claims, 19 Drawing Sheets
(19 of 19 Drawing Sheet(s) Filed in Color)

(51) Int. Cl.

| | |
|---|---|
| *A61B 1/31* | (2006.01) |
| *A61B 34/30* | (2016.01) |
| *A61M 25/01* | (2006.01) |
| *F04B 43/08* | (2006.01) |
| *F04B 43/12* | (2006.01) |
| *F04B 43/14* | (2006.01) |
| *A61B 34/32* | (2016.01) |
| *F04B 53/00* | (2006.01) |

(52) U.S. Cl.
CPC ......... *A61B 34/32* (2016.02); *A61M 25/0116* (2013.01); *F04B 43/08* (2013.01); *F04B 43/082* (2013.01); *F04B 43/088* (2013.01); *F04B 43/1292* (2013.01); *F04B 43/14* (2013.01); *A61B 1/31* (2013.01); *A61M 25/0122* (2013.01); *F04B 53/006* (2013.01)

(58) Field of Classification Search
CPC .............. F04B 27/0531; F04B 27/0619; F04B 27/0625; F04B 27/0631; F04B 27/0638; F04B 27/0644; F04B 27/0676; F04B 27/073; F04B 2201/1213
USPC ................................ 600/104, 106, 114–115; 604/95.01–95.05, 151–153; 417/53–55, 417/393–395, 474–476, 477.1–477.14
See application file for complete search history.

(56) References Cited

U.S. PATENT DOCUMENTS

| | | | |
|---|---|---|---|
| 3,221,702 A | | 12/1965 | Clark |
| 3,452,702 A | | 7/1969 | Slemmons |
| 3,623,566 A | | 11/1971 | Orloff |
| 3,964,316 A | | 6/1976 | Abe |
| 4,176,662 A | | 12/1979 | Frazer |
| 5,090,259 A | | 2/1992 | Shishido et al. |
| 5,318,413 A | * | 6/1994 | Bertoncini ........ A61M 5/14228 417/474 |
| 5,364,353 A | | 11/1994 | Corfitsen et al. |
| 5,662,587 A | | 9/1997 | Grundfest et al. |
| 5,846,064 A | * | 12/1998 | Refson .................... F04B 43/14 417/474 |
| 5,980,490 A | * | 11/1999 | Tsoukalis .............. F04B 43/082 417/474 |
| 6,007,482 A | | 12/1999 | Madni et al. |
| 6,029,294 A | | 2/2000 | Saringer |
| 6,702,735 B2 | | 3/2004 | Kelly |
| 6,764,441 B2 | | 7/2004 | Chiel et al. |
| 6,824,510 B2 | | 11/2004 | Kim et al. |
| 7,090,548 B1 | | 8/2006 | Gusler |
| 7,617,891 B2 | | 11/2009 | Chan et al. |
| 2003/0029257 A1 | | 2/2003 | Kerrebrock |
| 2005/0033343 A1 | | 2/2005 | Chermoni |
| 2006/0172625 A1 | | 8/2006 | Gusler |
| 2007/0079997 A1 | | 4/2007 | Chan et al. |
| 2007/0128060 A1 | * | 6/2007 | Miyazaki .............. F04B 43/082 417/474 |
| 2008/0193307 A1 | | 8/2008 | Elata et al. |
| 2010/0021315 A1 | * | 1/2010 | Wolff .................... F04B 43/082 417/53 |

OTHER PUBLICATIONS

Chen et al. "Analysis of Traveling Wave Locomotion of Snake Robot", Proceedings of the 2003 IEEE International Conference on Robotics, Intelligent Systems and Signal Processing, Changsha, China, Oct. 2003, p. 365-369, Oct. 2003.

Gabai et al. "Excitation and Sensing of Multiple Vibrating Traveling Waves in One-Dimensional Structures", Journal of Sound and Vibration, 319: 406-425, 2009.

Lauga et al. "The Hydrodynamics of Swimming Microorganisms", Reports on Progress in Physics, 72: 096601-1-096601-36, 2009.

Manceau et al. "On the Generation and Identification of Traveling Waves in Non-Circular Structures—Applications to Innovative Piezoelectric Motors", Smart Materials and Structures, 7: 337-344, 1998.

Minikes et al. "Levitation Force Induced by Pressure Radiation in Gas Squeeze Films", Journal of the Acoustical Society of America, 116(1): 217-226, Jul. 2004.

Minikes et al. "Noncontacting Lateral Transportation Using Gas Squeeze Film Generated by Flexural Traveling Waves—Numerical Analysis", Journal of the Acoustical Society of America, 113(5): 2464-2473, May 2003.

Setter et al. "Flexural Vibration Patterning Using an Array of Actuators", Journal of Sound and Vibration, 330: 1121-1140, 2011.

* cited by examiner

FIG. 12A
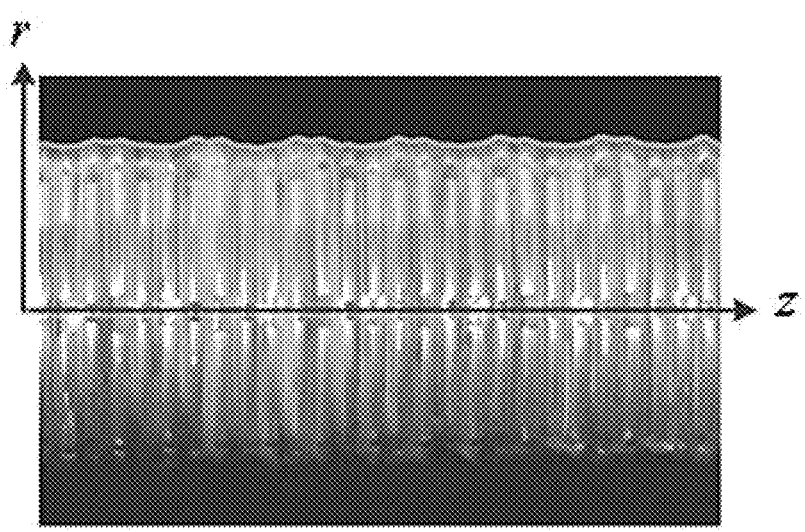
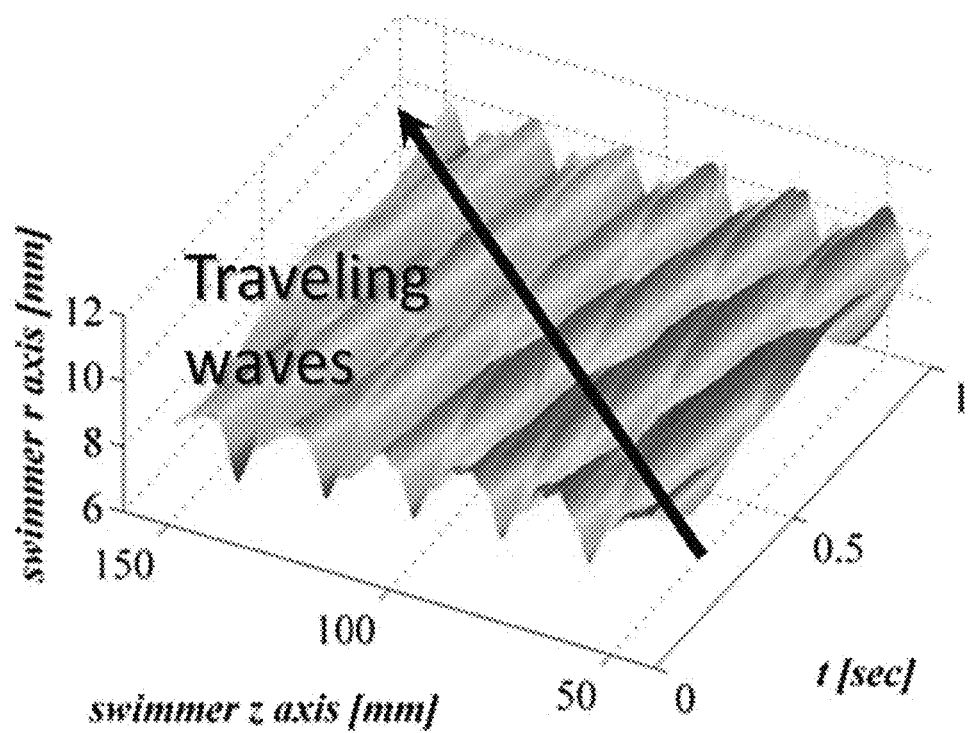
FIG. 12B

FIG. 14
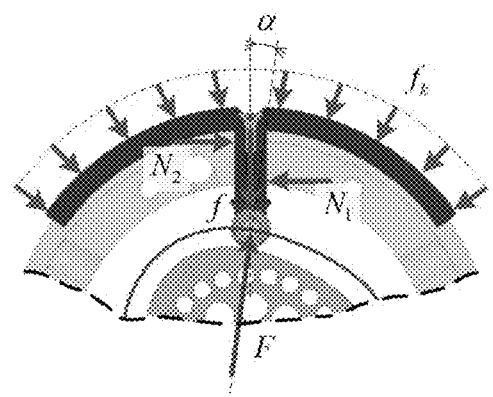
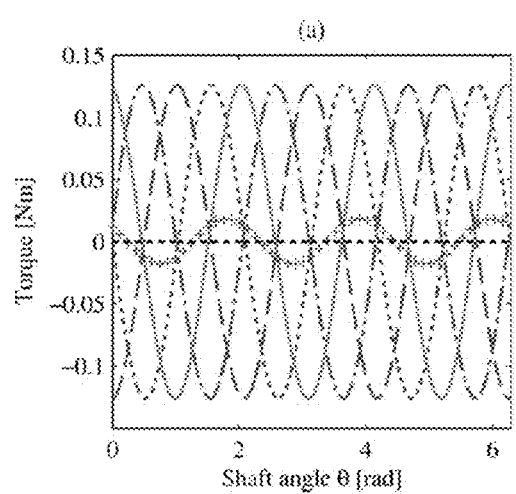
FIG. 15A
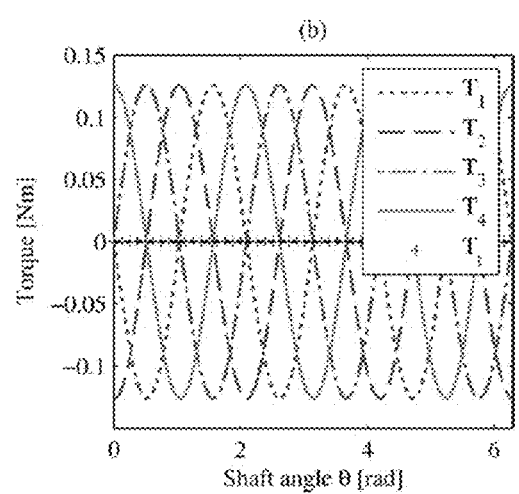
FIG. 15B

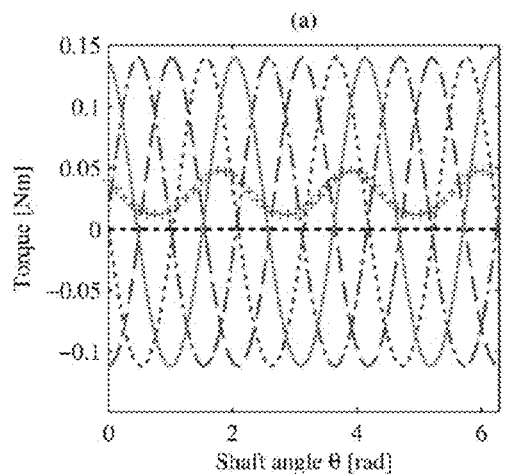 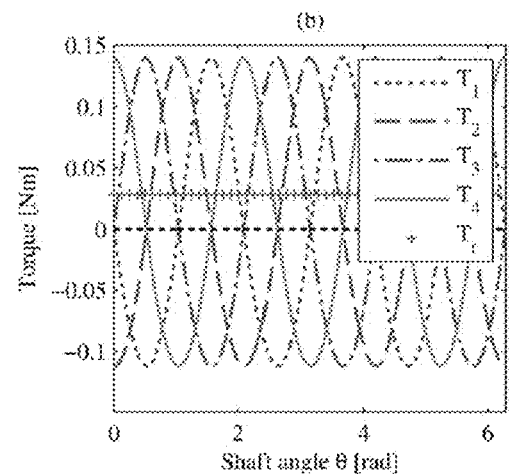
FIG. 16A  FIG. 16B
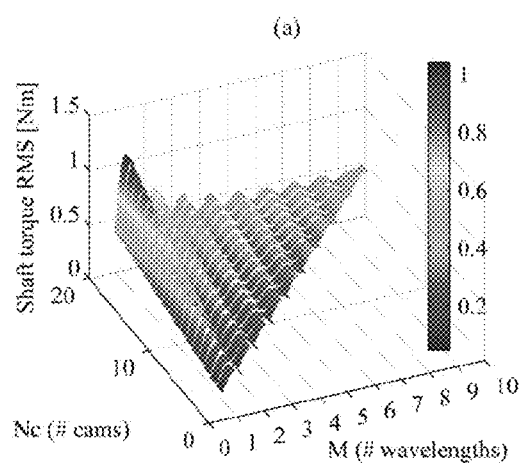 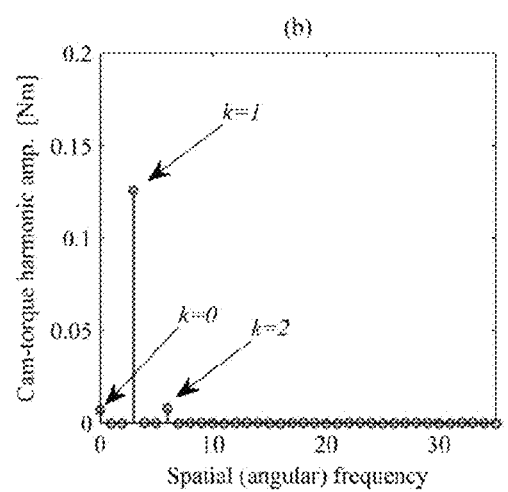
FIG. 17A  FIG. 17B

METHOD AND SYSTEM FOR GENERATING MECHANICAL WAVES

RELATED APPLICATION

This application claims the benefit of priority under 35 USC 119(e) of U.S. Provisional Patent Application No. 61/601,629 filed Feb. 22, 2012, the contents of which are incorporated herein by reference in their entirety.

FIELD AND BACKGROUND OF THE INVENTION

The present invention, in some embodiments thereof, relates to mechanical waves and, more particularly, but not exclusively, to a method and system for generating mechanical waves, useful, e.g., for the locomotion of autonomous vehicles and/or fluids.

The ability to move through long, flexible and curved tubes has long been a challenge for engineers since numerous applications can benefit from a reliable solution. This ranges from medical applications for treatment and diagnosis to sewer pipes, gas pipes and power plants.

In search for a solution, a number of locomotion types of propulsion have been developed, which pull at the distal end of the lumen rather than pushing at the proximal end. Examples in non-medical applications include crawling vehicles and spider-like robots, such as are described in U.S. Pat. Nos. 6,824,510 and 5,090,259.

In medical applications the most common solution is that of the inch worm type, that advances by means of peristaltic motion, such as is described, for instance, in U.S. Pat. Nos. 6,764,441, 4,176,662, 5,090,259, 5,662,587, 6,007,482 and 5,364,353. Another type of medical application device is described in U.S. Pat. No. 6,702,735. An additional solution is one which uses motion hydraulically generated close to the tip, such as is described in U.S. Published Application No. 20050033343.

Another type of self-propelled system is a robot that employs low frequency, non-vibratory, traveling waves as described in U.S. Published Application No. 20030029257, and in Li et al., 2003, "Analysis of traveling wave locomotion of snake robot," in Robotics, Intelligent Systems and Signal Processing, 2003. Proceedings 2003 IEEE International Conference on, 365-369 vol. 1. A snail-like robot is disclosed in U.S. Published Application No. 20070079997 and in Chan et al., 2005, "Building a better snail: Lubrication and adhesive locomotion," Physics of Fluids, vol. 17.

Also of interest are U.S. Pat. Nos. 3,221,702, 3,154,043, 3,066,637 and 3,623,566, and U.S. Published Application No. 20060172625, which are directed to the use of slow non-vibratory traveling waves to propel vehicles, and U.S. Pat. Nos. 6,029,294 and 3,964,316 which are directed to wave generators for therapeutic use and ocean waves simulator, respectively.

Additional background art includes E. Setter and I. Bucher (2011) "Flexural vibration patterning using an array of actuators," Journal of Sound and Vibration, vol. 330, 1121-1140; R. Gabai and I. Bucher, 2009, "Excitation and sensing of multiple vibrating traveling waves in one-dimensional structures," Journal of Sound and Vibration, vol. 319, 406-425; S. Ueha and Y. Tomikawa, 1993, "Ultrasonic Motors: Theory and Applications, with contributions from M. Kurosawa and N. Nakamura," Oxford, Clarendon Press; Jean-François et al., 1998, "On the generation and identification of traveling waves in non-circular structures—application to innovative piezoelectric motors," Smart Materials and Structures, vol. 7, 337; A. Minikes and I. Bucher, 2003, "Noncontacting lateral transportation using gas squeeze film generated by flexural traveling waves—Numerical analysis," Journal of the Acoustical Society of America, vol. 113, 2464-2473; and Minikes et al., 2004, "Levitation force induced by pressure radiation in gas squeeze films," Journal of the Acoustical Society of America, vol. 116, 217-226.

SUMMARY OF THE INVENTION

According to an aspect of some embodiments of the present invention there is provided a system for generating mechanical waves. The system comprises: a camshaft having plurality of rotatable cams, serially mounted on a shaft along an axis of an elastic tubular shell to form a varying phase angle along the shaft. The system further comprises a plurality of cam followers arranged circumferentially about each cam, such that a rotary motion of the cams generates a linear motion of the cam followers to radially bias in internal wall the shell. The variation of the phase angle is selected to generate a three-dimensional traveling wave along the shell.

According to some embodiments of the invention the variation of the phase angle is selected such that a variation of a torque on the shaft during the rotation is below a predetermined threshold.

According to some embodiments of the invention the system further comprising a plurality of arcs respectively mounted on the plurality of cam followers, such that the arcs engage the internal wall during at least part of the linear motion.

According to some embodiments of the invention a number and separation of the cams along the shaft is selected such that $kL/\lambda$ is generally an integer, where k is an integer, L is a length of the camshaft and $\lambda$ is a wavelength of the wave. According to some embodiments of the invention a number and separation of the cams along the shaft is selected such that $kL/(\lambda Nc)$ is non-integer.

According to some embodiments of the invention the plurality of cam followers comprises three cam followers per cam. According to some embodiments of the invention the plurality of cam followers comprises four cam followers per cam. According to some embodiments of the invention the plurality of cam followers comprises five cam followers per cam. According to some embodiments of the invention the plurality of cam followers comprises six cam followers per cam. According to some embodiments of the invention the plurality of cam followers comprises more than six cam followers per cam.

According to some embodiments of the invention the system further comprising a motor operatively connected to the shaft and communication device for remote activation, control and deactivation of the motor.

According to some embodiments of the invention at least one of the cams has a single-harmonic profile.

According to some embodiments of the invention at least one of the cams has a multi-harmonic profile.

According to an aspect of some embodiments of the present invention there is provided an autonomous self-propelled vehicle. The vehicle comprises the system for generating mechanical waves, as delineated above and optionally as further detailed below.

According to some embodiments of the invention the vehicle is adapted for being introduced into a body lumen of a mammal.

According to some embodiments of the invention the vehicle is adapted for being introduced into a structure selected from the group consisting of a pipe, a channel, a building duct, a borehole and a pool.

According to an aspect of some embodiments of the present invention there is provided a self-propelled endoscope system. The endoscope system comprises the system for generating mechanical waves, as delineated above and optionally as further detailed below.

According to an aspect of some embodiments of the present invention there is provided a pump. The pump comprises the system for generating mechanical waves, as delineated above and optionally as further detailed below.

According to an aspect of some embodiments of the present invention there is provided a method of displacing an object. The method comprises introducing a self-propelled vehicle having the object into a fluid medium. In various exemplary embodiments of the invention the self-propelled vehicle comprises: a camshaft having plurality of rotatable cams, serially mounted on a shaft along an axis of an elastic tubular shell to form a varying phase angle along the shaft; and a plurality of cam followers arranged circumferentially about each cam, such that a rotary motion of the cams generate a linear motion of the cam followers to radially bias in internal wall the shell; wherein the variation of the phase angle is selected to generate a three-dimensional traveling wave along the shell.

According to some embodiments of the invention the fluid medium is characterized by a Reynolds number less than 1.

According to some embodiments of the invention the fluid medium is in a body lumen of a mammal.

According to some embodiments of the invention the body lumen selected from the group consisting of a vein, an artery, a gastrointestinal tract and a colon.

According to some embodiments of the invention the fluid medium is contained in a structure selected from the group consisting of a pipe, a channel, a building duct, a borehole and a pool.

According to some embodiments of the invention the object is at least one of: a drug, a camera, a distal end of an endoscope, a sensor, a communication device, a sent, an electrical stimulation device, and a magnetic stimulation device.

According to an aspect of some embodiments of the present invention there is provided a method of pumping. The method comprises fixating a pump system in a lumen having a fluid medium therein and activating the pump. In various exemplary embodiments of the invention the pump system comprises a camshaft having plurality of rotatable cams, serially mounted on a shaft along an axis of an elastic tubular shell to form a varying phase angle along the shaft; and a plurality of cam followers arranged circumferentially about each cam, such that a rotary motion of the cams generate a linear motion of the cam followers to radially bias in internal wall the shell; wherein the variation of the phase angle is selected to generate a three-dimensional traveling wave along the shell.

According to some embodiments of the invention a smallest dimension of the shell is at least 1 centimeter, and wherein the fluid is liquid having a viscosity of at least 10000 cSt.

According to some embodiments of the invention a smallest dimension of the shell is from about 1 mm to about 1 centimeter, and wherein the fluid is liquid having a viscosity of at least 1 cSt.

According to some embodiments of the invention the fluid is body liquid.

According to some embodiments of the invention the fluid is a biological fluid.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic illustration of a system for generating mechanical waves, according to some embodiments of the present invention;

Figure 2A:
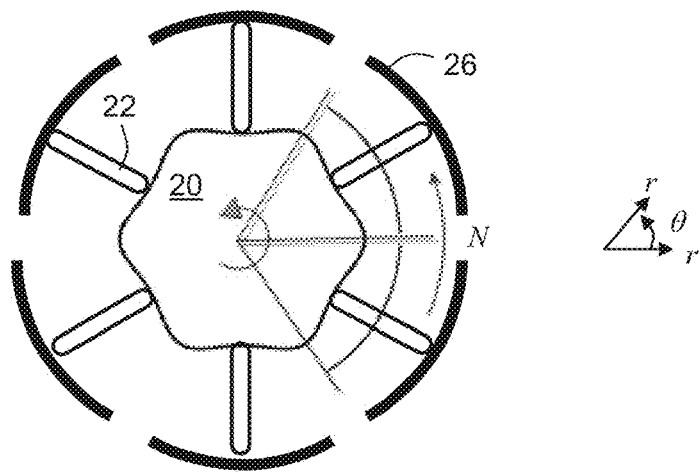
Figure 2B:
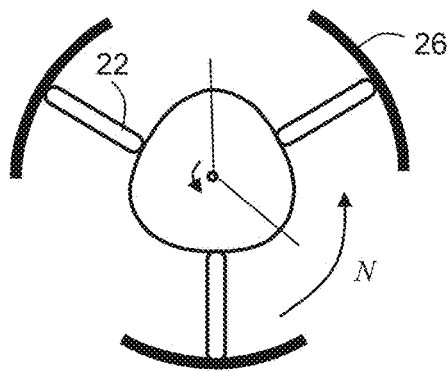
Figure 2C:
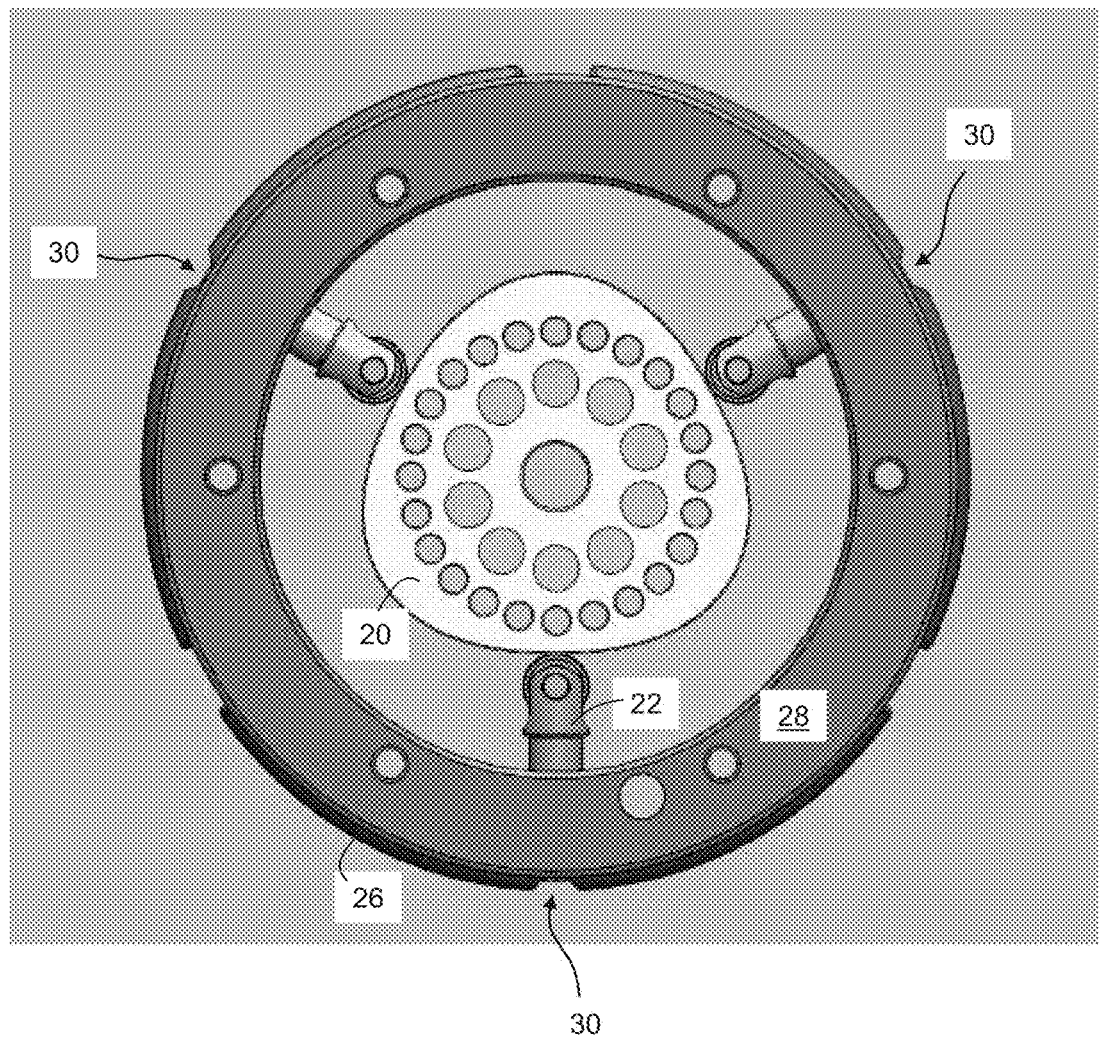
Figure 3:
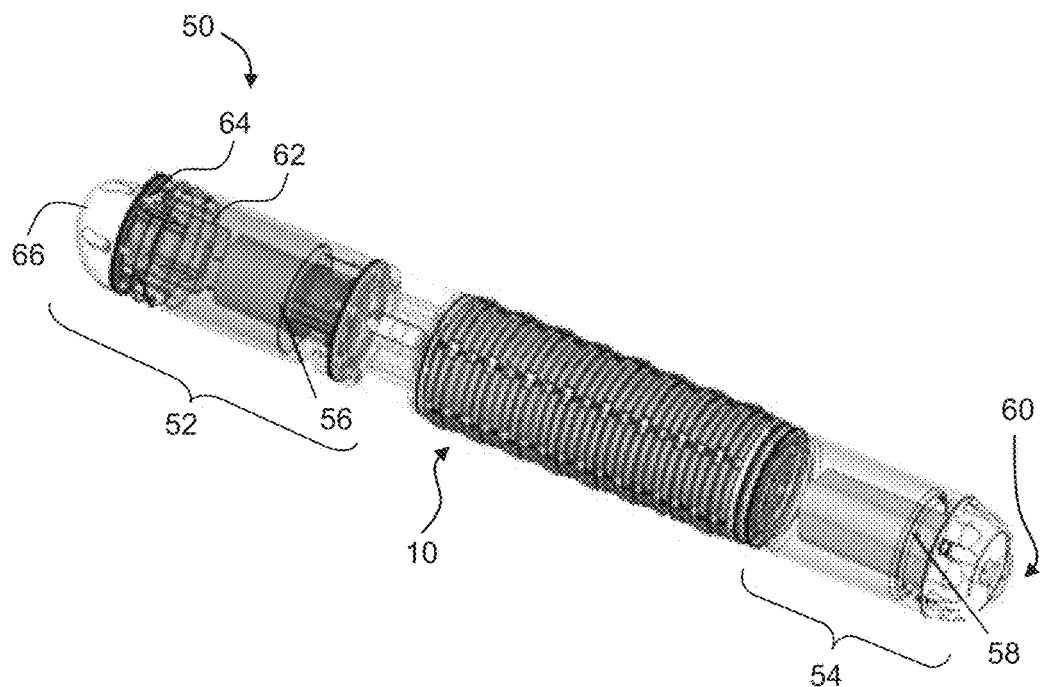
Figure 4:
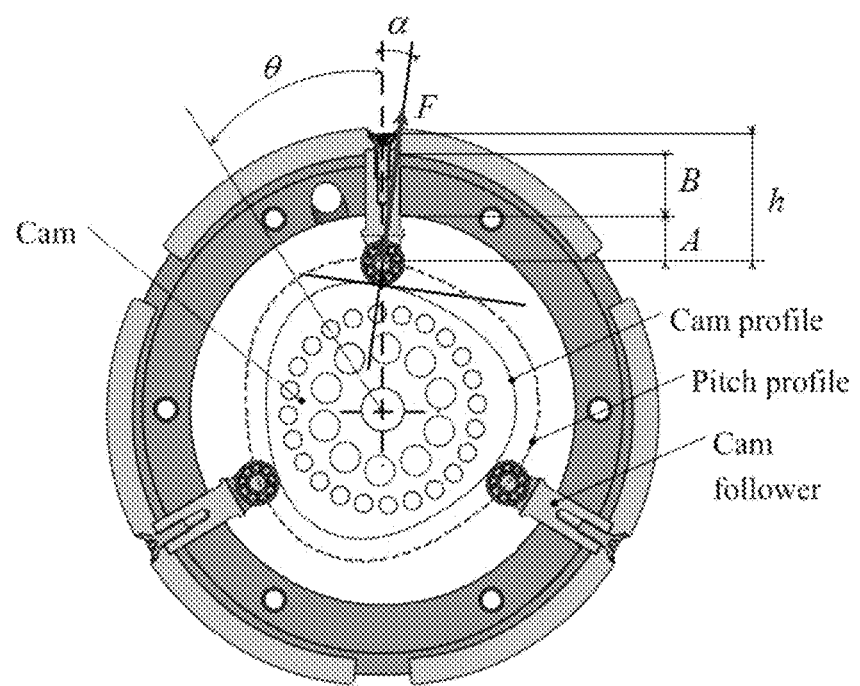
Figure 5A:
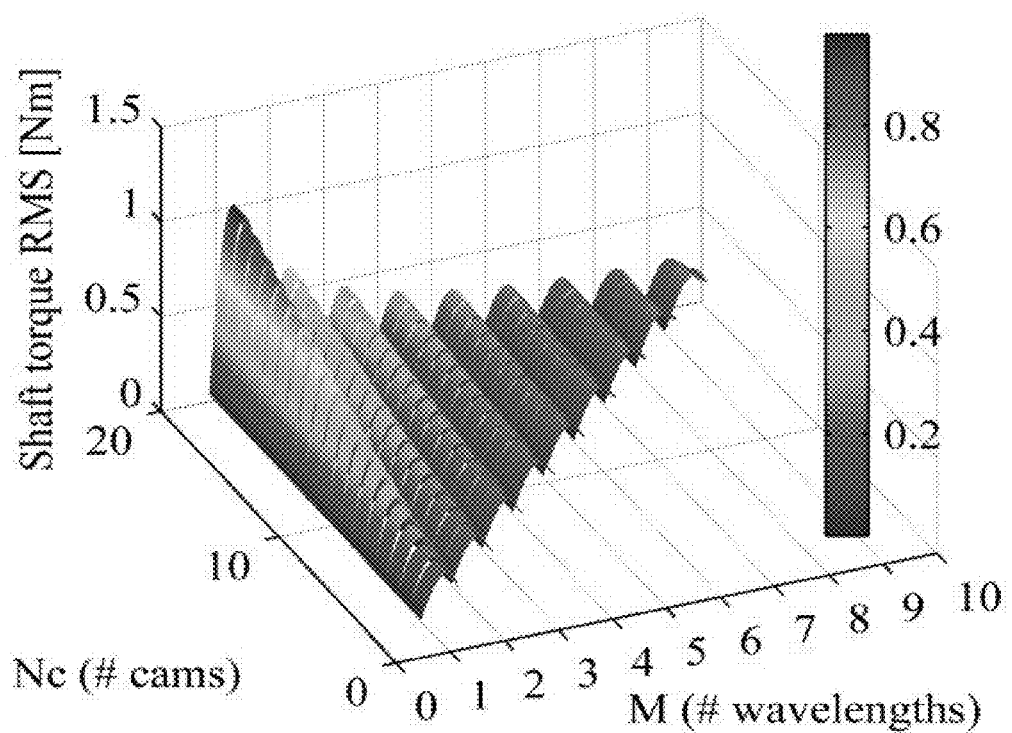
Figure 5B:
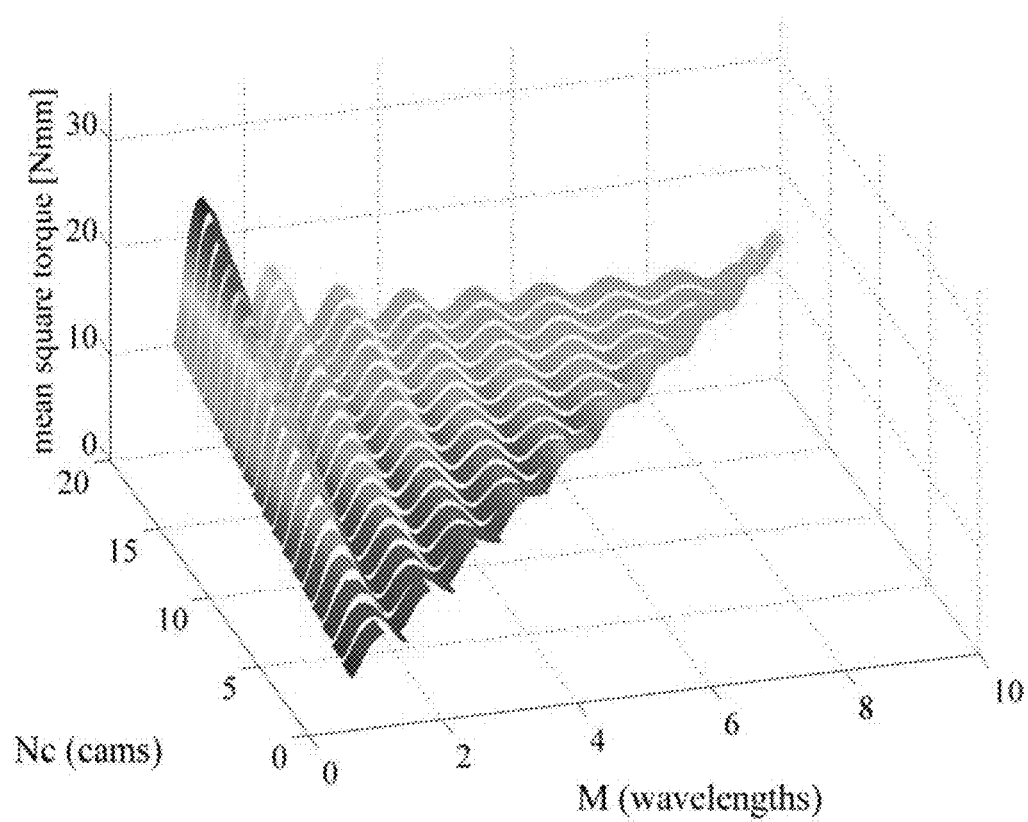
Figure 6A:
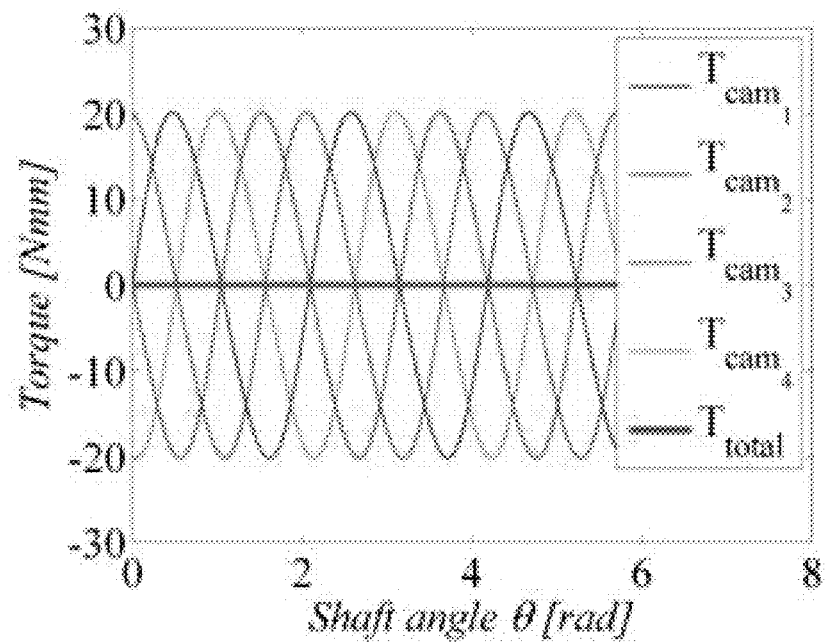
Figure 6B:
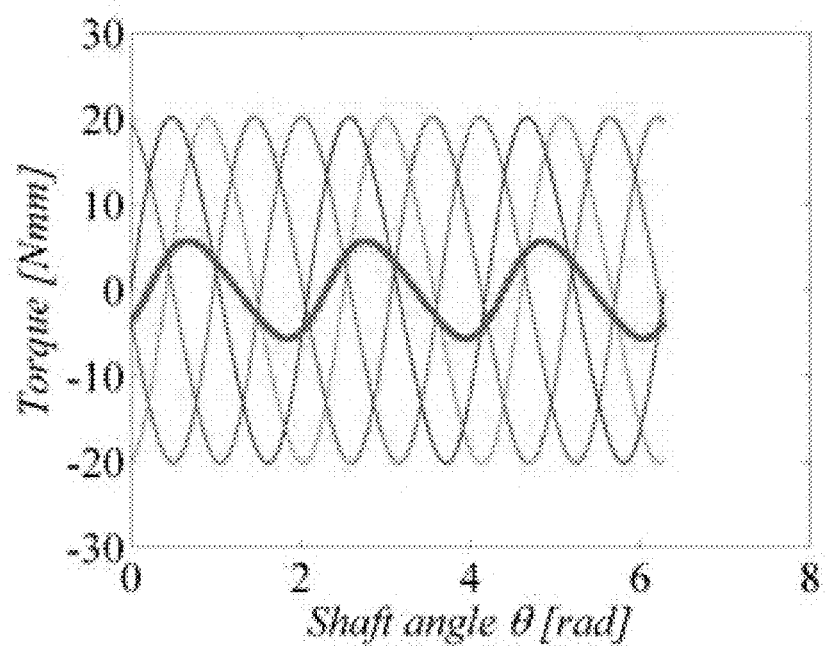
Figure 6C:
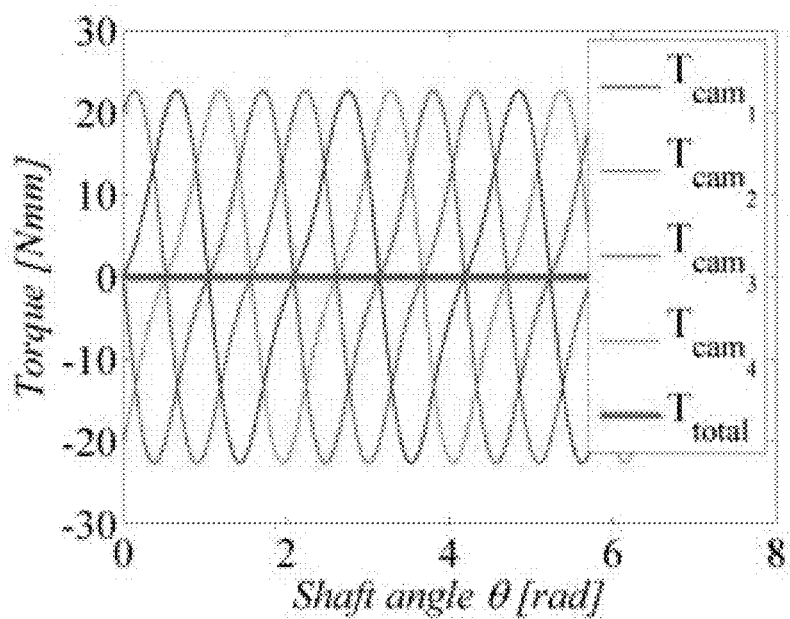
Figure 6D:
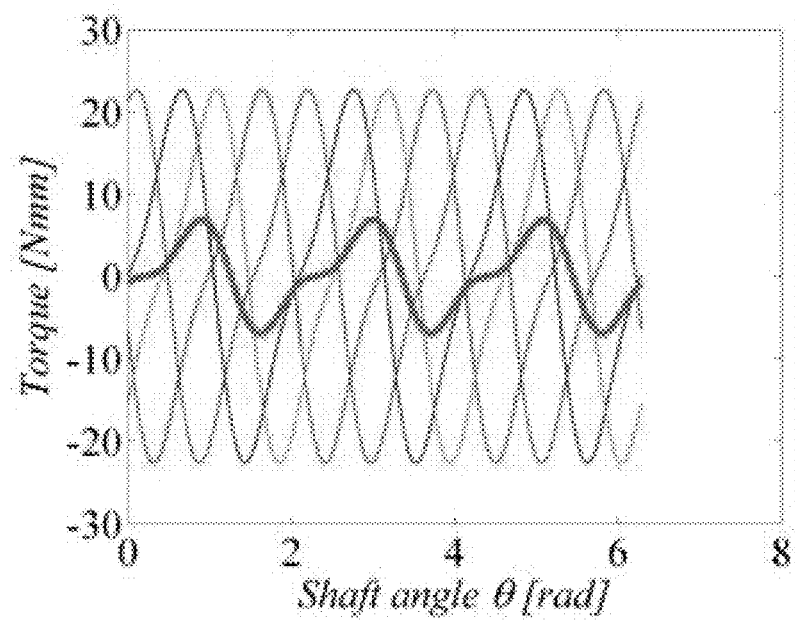
Figure 9A:
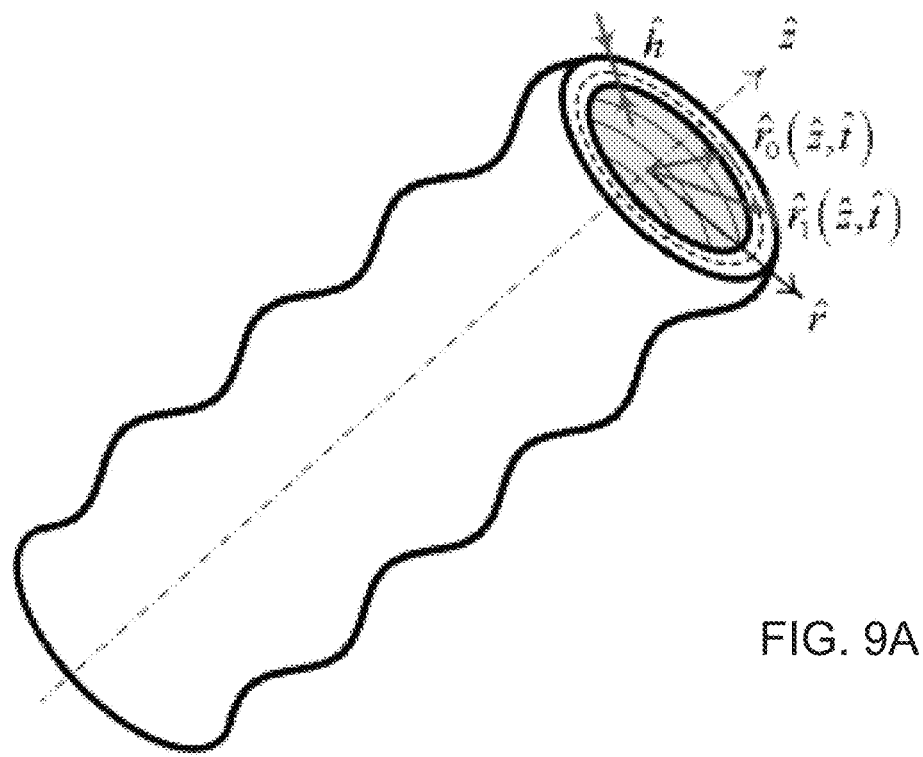
Figure 9B:
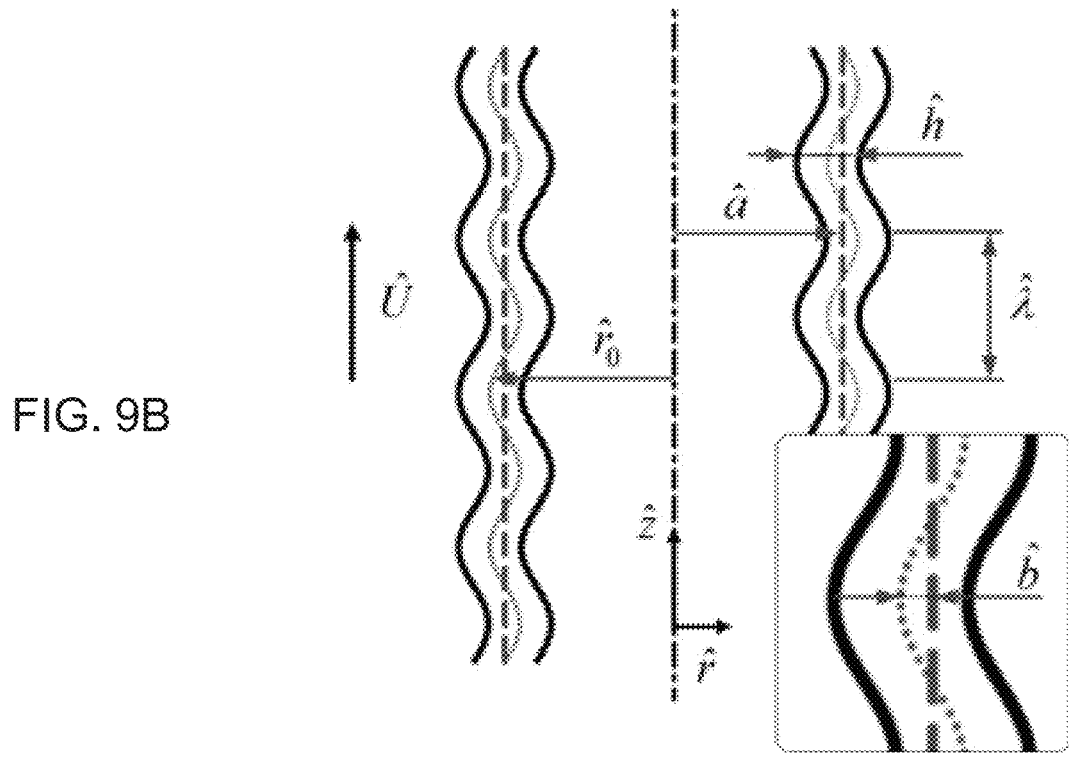
Figure 10:
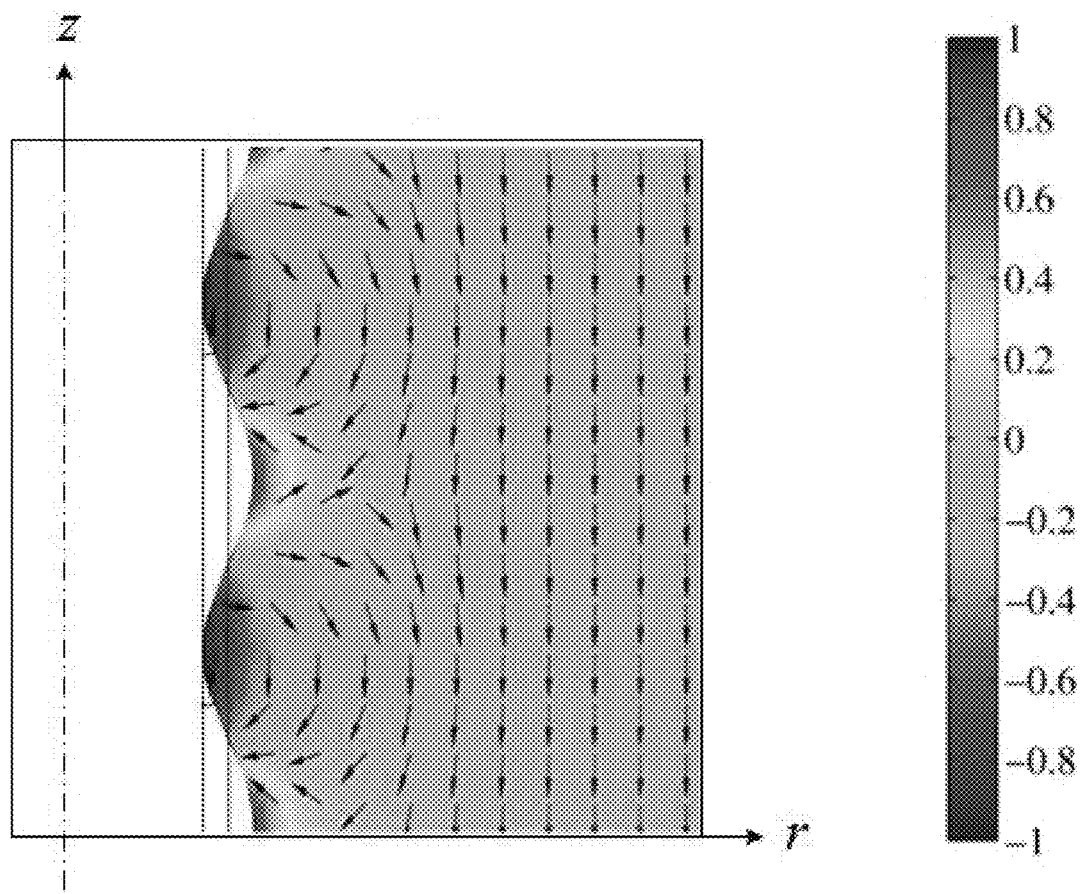
Figure 11:
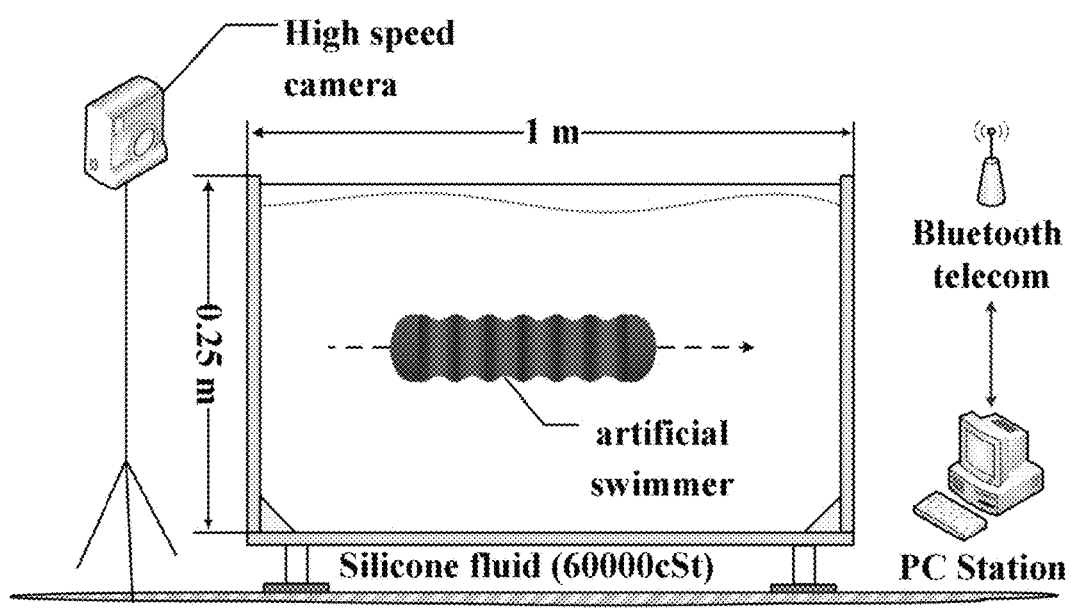
Figure 13:
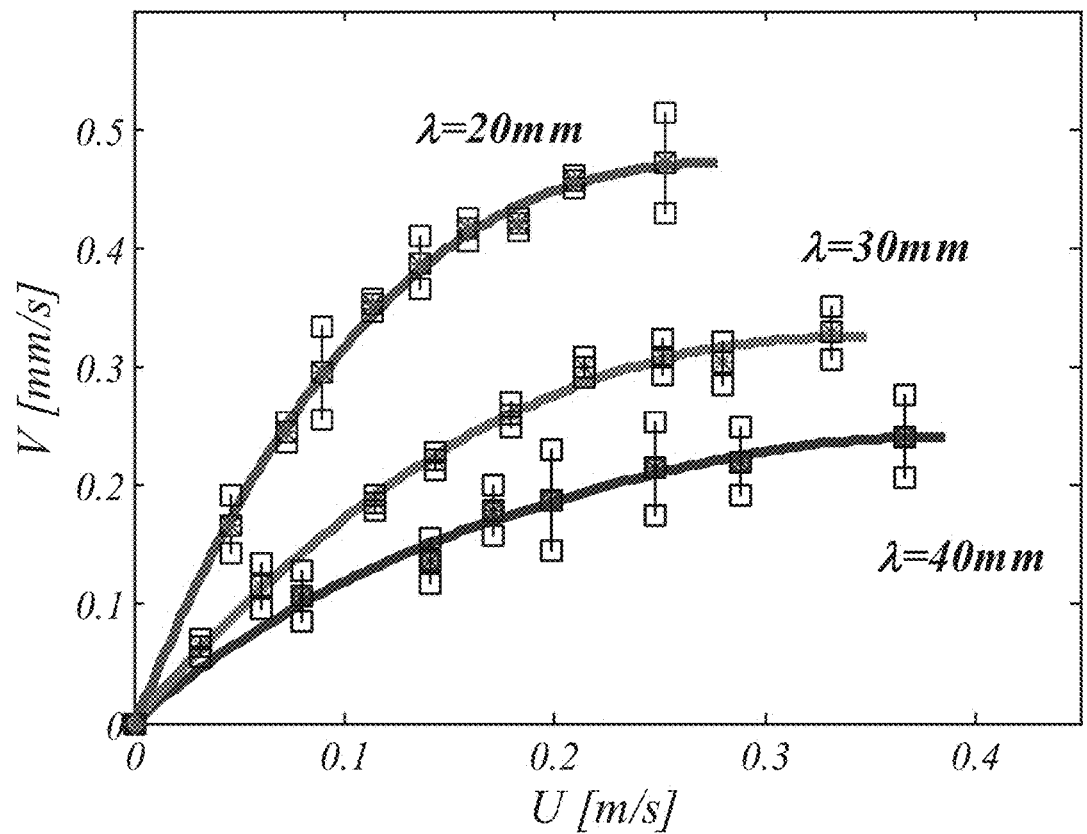
Figure 18A:
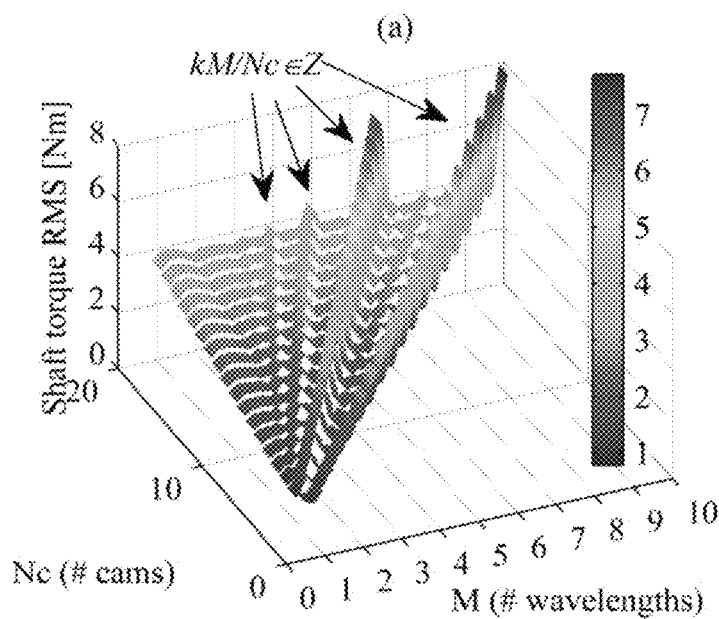
Figure 18B:
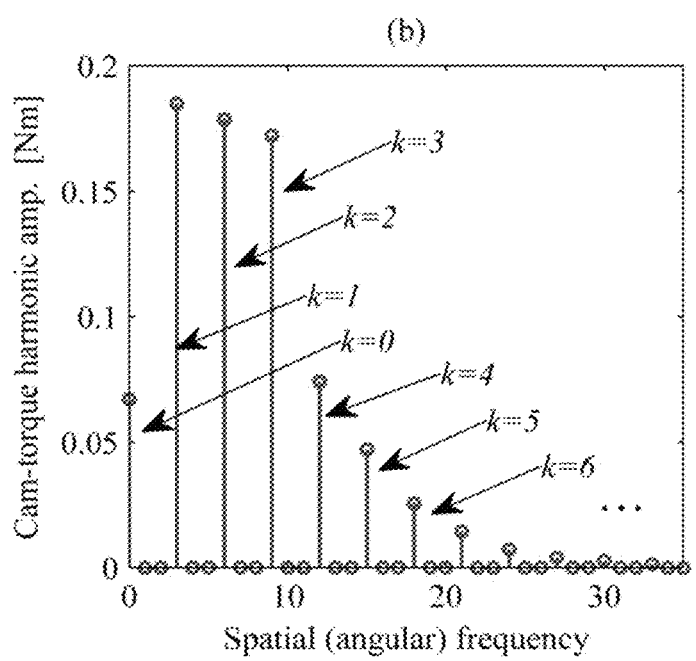

FIGS. 2A-B are schematic illustration of representative examples of cam profiles, suitable for some embodiments of the present invention;

FIG. 2C is a schematic illustration of a representative example of a structural relation between a cam, cam followers, and arcs according to some embodiments of the present invention;

FIG. 3 is a schematic illustration of a system which incorporates a system for generating mechanical waves, and which can be used as an autonomous self-propelled vehicle or a pump, according to some embodiments of the present invention;

FIG. 4 is a schematic illustration of a cam profile and a corresponding pitch profile generated during the rotation of the cam;

FIGS. 5A-B show mean squared torque integrated over one shaft revolution, as obtained during computer simulation performed according to some embodiments of the present invention;

FIGS. 6A-D show the effect of a phase shift between cams on a torque, obtained during computer simulation performed, according to some embodiments of the present invention, for a case of negligible friction;

FIGS. 7A-D show the effect of a phase shift between cams on a torque, obtained during computer simulation performed, according to some embodiments of the present invention, for a case of non-negligible friction;

FIGS. 8A-D show the effect of non-negligible cam followers inertia, as obtained during computer simulation performed according to some embodiments of the present invention, using a harmonic decomposition of the torque signal;

FIGS. 9A-B are schematic illustrations of a swimmer system, used in a computer simulations performed according to some embodiments of the present invention;

FIG. 10 shows vorticity field adjacent to the wave generating system, as obtained during computer simulation performed according to some embodiments of the present invention;

FIG. 11 is a schematic illustration of an experimental system used in experiments performed according to some embodiments of the present invention;

FIG. 12A shows a still image of a prototype system, with an emphasized detected edge (cyan) of the wave generated along a shell of the system, as obtained during experiments performed according to some embodiments of the present invention;

FIG. 12B shows tempo-spatial representation of the a wave generated along the shell of a prototype system envelope, as obtained during experiments performed according to some embodiments of the present invention;

FIG. 13 shows velocity of a prototype system recorded for several wavelengths and wave velocities, as obtained during experiments performed according to some embodiments of the present invention;

FIG. 14 illustrates forces acting on a cam follower of a system according to some embodiments of the present invention;

FIGS. 15A-B show curves of torque load on four successive cams and a resultant torque on a shaft, as a function of the rotation angle, for deviated (FIG. 15A) and non-deviated phase shift (FIG. 15B), obtained during computer simulation performed according to some embodiments of the present invention, for a case of negligible dissipative losses;

FIGS. 16A-B show curves of torque load on four successive cams and a resultant torque on a shaft, as a function of the rotation angle for, for deviated (FIG. 16A) and non-deviated phase shift (FIG. 16B), obtained during computer simulation performed according to some embodiments of the present invention for a case of finite viscous damping and negligible Coulomb friction;

FIGS. 17A-B show RMS of shaft torque as a function of the number of cams and number of wavelengths in the shell (FIG. 17A), and Harmonic decomposition of the spatial (angular) frequencies of the torque load on a single cam (FIG. 17B), as obtained during computer simulation performed according to some embodiments of the present invention for a case of finite viscous damping and negligible Coulomb friction; and FIGS. 18A-B show RMS of shaft torque as a function of the number of cams and number of wavelengths in the shell (FIG. 18A), and Harmonic decomposition of the spatial (angular) frequencies of the torque load on a single cam (FIG. 18B), as obtained during computer simulation performed according to some embodiments of the present invention for a case of finite Coulomb friction and multi-harmonic cam profile.

DESCRIPTION OF SPECIFIC EMBODIMENTS OF THE INVENTION

The present invention, in some embodiments thereof, relates to mechanical waves and, more particularly, but not exclusively, to a method and system for generating mechanical waves, useful, e.g., for the locomotion of autonomous vehicles and/or fluids.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Traveling mechanical waves can be utilized for inducing transport, particularly under low Reynolds number conditions (e.g., small scale spaces or highly viscous liquids), where the dynamics is mainly governed by drag effects, and the present inventor recognized that propulsion can be maintained only by non-inertial and non-time-reversible trajectories.

It was recognized by the present inventors that since pure vibratory traveling waves do not always occur in resonance, a conventional wave based actuation system is energetically inefficient due to the elastic and inertial forces that have to be overcome. In a search for a solution to the problem of locomotion of autonomous vehicles and/or fluids, particularly at low Reynolds number conditions (e.g., Reynolds number less than 1 or less than 0.9 or less than 0.8 or less than 0.7 or less than 0.6 or less than 0.5 or less than 0.4 less than 0.3 or less than 0.2 or less than 0.1), the present inventors devised a system for generating mechanical waves, referred to herein as system 10.

Figure 1:
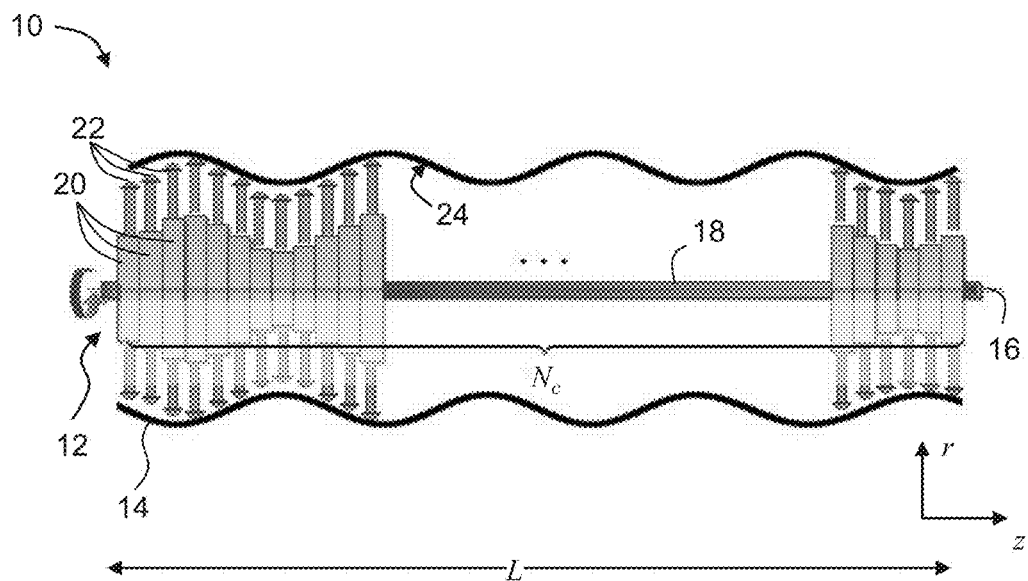

Referring now to the drawings, FIG. 1 illustrates system 10, according to some embodiments of the present invention. System 10 preferably comprises a camshaft 12 positioned in an elastic tubular shell 14, which optionally and preferably has a cylindrical symmetry along a symmetry axis 16. For example, shell 14 can have a shape of a cylinder. Shell 14 can be made of any material of sufficient elasticity. Typically, but not necessarily, the elasticity modulus of shell 14 is at least 100 Pa or at least 1 kPa or at least 1 MPa. A representative example of a material suitable for shell 14 includes, without limitation, a natural latex rubber or another material, optionally and preferably of similar mechanical characteristics. Preferably, but not necessarily, shell 14 is made of a biocompatible elastic material. Shell 14 can be structured as a rolled sheet or it can be made of woven or nonwoven fibers.

Camshaft 12 comprises a plurality of rotatable cams 20, serially mounted on a shaft 18 along axis 16 of tubular shell 14. The number of cams in camshaft 12 is denoted $N_c$ and the distance between the first and last cams of camshaft 12 is referred to as the length L of camshaft 12 (although shaft 18 may be longer than L). Cams 20 are optionally and preferably identical to each other. Each cam has a flat shape, typically planar, with a rotation axis which is coaxial with shaft 18, wherein the shape of the periphery of the cam (referred to herein as the cam profile) and the position of rotation axis are such that the distance between the rotation axis and the periphery varies along the periphery. Preferably, cams 20 have a generally smooth profile. Representative examples of cam profiles, which are not to be considered as limiting, are illustrated in FIGS. 2A-B. The number of angular wavelengths along the periphery of cam 20 is denoted N. FIG. 2A illustrates an embodiment in which N=6 and FIG. 2B illustrates an embodiment in which N=3.

The cam profile can be of a single harmonic type or multi-harmonic type, as desired.

As used herein, a "single harmonic profile," refers to a profile that can be expressed mathematically using a single basic trigonometric function, such as a cosine function or a sine function.

As used herein, a "multi harmonic profile," refers to a profile that cannot be expressed mathematically using a single basic trigonometric function, such as a cosine function or a sine function, and that can only be expressed mathematically using two or more periodic functions each featuring a different periodicity.

A single harmonic cam profile is particularly useful when it is desired to generate a single-wavelength mechanical wave, and a multi-harmonic cam profile is particularly useful when it is desired to generate a complex mechanical wave.

As used herein, "complex mechanical wave" refers to a mechanical wave which is described mathematically as a superposition of two or more wave functions each having a single wavelength and a single frequency.

Representative examples of complex mechanical waves including, without limitation, a mechanical wave resembling a triangular wave, a mechanical wave resembling a square wave, a mechanical wave resembling a saw-tooth wave, and a mechanical wave resembling a wavelet.

The coordinates of the various components of system 10 are conveniently described using a cylindrical coordinate system, in which the longitudinal direction is denoted by z and is collinear with axis 16, the radial direction is denoted by r, and the azimuthal angle is denoted θ. Thus, FIG. 1 is along the z-r plane and FIGS. 2A-B are along the r-θ plane.

System 10 further comprises a plurality of cam followers 22 arranged circumferentially about each cam 20, such that a rotary motion of cams 20 generates a linear reciprocating motion of cam followers 22 in the radial direction. The amplitude of the reciprocating motion is selected to allow cam followers 22 to radially bias the internal wall 24 of shell 14. Cam followers 22 can be of any type and material suitable for converting a rotary motion to a linear motion. In some embodiments, system 10 comprises a plurality of arcs 26, respectively mounted on cam followers 22, such the arcs 26 engage internal wall 24 during at least part of the linear motion of cam followers 22. In various exemplary embodiments of the invention arcs 26 engage internal wall 24 during the entire linear motion of cam followers 22.

A representative example of a relation between cam 20, cam followers 22, and arcs 26 according to some embodiments of the present invention is illustrated in FIG. 2C. In this configuration, cam 20 is positioned in a ring element 28 having a plurality of bores 30 configured for receiving the cam followers 22, one cam followers 22 per bore. Bores 30 are oriented along the radial direction, and therefore serve for constraining the motion of cam followers 22 to the radial direction. Cam followers 22 move together with arcs 26.

The number of cam followers per cam can vary. In some embodiments of the present invention the number of cam followers per cam equals the number N of axial wavelengths along the periphery of the cam, but need not necessarily be the case, since, for some applications, it may not be necessary for the number of cam followers per cam to match the number of angular wavelengths along the periphery of the cam.

The orientation of the cams is selected to form a varying phase angle along shaft 18. For example, each cam can be oriented at an angle θ which is shifted with respect to the orientation of the cam adjacent thereto. Typically, but not necessarily, there is a constant shift Δθ in the phase angle between any two successive cams. In various exemplary embodiments of the invention the variation of the phase angle is selected to generate a three-dimensional traveling wave along shell 14. For example, when a constant shift Δθ is employed, a traveling wave having a wavelength λ can be achieved by selecting Δθ to be about $2\pi M/(N \cdot N_c)$ where $M=L/\lambda$ is the number of wavelengths along the length of camshaft 12.

Thus, as camshaft 12 rotates, cam-followers 22 reciprocate radially, altering the diameter of shell 14 periodically in a predetermined order, to provide a mechanical traveling wave of deformation along shell 14, traveling in the direction of axis 16.

It was found by the present inventors that the relations between at least some of the elements of system 10 can be selected to significantly reduce the variations of the torque on shaft 18. In some embodiments of the present invention, the variation of the phase angle along shaft 18 is selected such that the variation of the torque on shaft 18 during the rotation is below a predetermined threshold. A typical value for the predetermined threshold is about 20% or about 10% or about 5% or about 2% per cycle of rotation.

It was found by the present inventors that the variation of the torque is sensitive to the selection of shifts of phase angles among cams, so that a small change of the phase shifts effects large changes on the extent of variations. For example, it was found by the present inventors that when a constant shift Δθ is employed, low variations of the torque can be achieved by selecting the value of Δθ to be in the range of from $2\pi M/(N \cdot N_c)-X$ to $2\pi M/(N \cdot N_c)+X$, where X is less that 10°/N, more preferably less than 9°/N, more preferably less than 8°/N, more preferably less than 7°/N, more preferably less than 6°/N, more preferably less than 5°/N, more preferably less than 4°/N, more preferably less than 3°/N, more preferably less than 2°/N, more preferably less than 1°/N, more preferably less than 0.5°/N.

It was additionally found by the present inventors that the mean value of the torque on shaft 18 can be significantly reduced, by exploiting the restoring force exerted by shell 14 on cam followers 22. Thus, in various exemplary embodiments of the invention the relation between the number $N_c$ of cams 20 and the parameter $M=L/\lambda$ is selected such that cam followers 22 do work on shell 14 only during part of the rotation cycle (typically half of the cycle), wherein in the other part of the cycle, shell 14 does work on cam followers 22 by exerting a restoring force thereon. This can be achieved, according to some embodiments of the present invention by selecting the number and separation of cams 20 along shaft 18 such that $kL/\lambda$ is generally an integer, and, optionally and preferably $kL/(\lambda N_c)$ is non-integer, where k is a positive integer which is less than or equal to a predetermined parameter K. Preferably, $kL/(\lambda Nc)$ is non-integer for any k in the series k=1, 2, . . . , K. Typically, K is not higher than the highest index in a Fourier expansion of the torque for which the respective harmonic has a magnitude which is higher than 5% of the mean torque magnitude. In some embodiments of the present invention K=3, in some embodiments K=4, in some embodiments K=5, in some embodiments K=6, in some embodiments K=7, in some embodiments K=8, in some embodiments K=9, in some embodiments K=10, and in some embodiments K>10.

FIG. 3 is a schematic illustration of a system 50 which incorporates system 10, and which can be used as an autonomous self-propelled vehicle or a pump. System 50 preferably comprises one or more casings 52, 54 for holding a motor 56 operatively connected to shaft 18 of system 10 so as to establish the rotary motion of shaft 18 with cams 20. Motor 56 is optionally and preferably an electrical motor powered by, e.g., DC voltage. The casings can also encapsulate a mobile power source 58 for powering motor 56. Power source 58 can include replaceable batteries and/or rechargeable batteries as known in the art. When power source 58 is of a rechargeable type, a recharge port 60 can be formed in casing 52 or 54. Casing 52 or 54 can also encapsulate a communication device 62 such as a Bluetooth® communication device or the like configured for remote activation, control and deactivation of motor 56.

In some embodiments of the present invention Casing 52 or 54 can also encapsulate a motion sensor 64, such as an accelerometer, preferably a 3-axis accelerometer. These embodiments are particularly useful when system 50 is embodied as an autonomous self-propelled vehicle in which case motion sensor can measure the motion characteristics of system 50 and transmit them, e.g., using communication device 62, to a remote location (not shown). Communication device 62 can also be configured to communicate with an external position tracking system (not shown) for determining the position of system 50.

Before providing a further detailed description of the system according to various exemplary embodiments of the present invention, attention will be given to the advantages and potential applications offered thereby.

The system of the present embodiments can be used for the locomotion of autonomous vehicles and/or fluids.

The term "fluid," as used herein, encompasses a liquid, a gas, and any other composition, mixture, or material exhibiting fluid behavior. The fluid may include a liquid, or a gas or gaseous mixtures. As used herein, the term fluid may encompass liquids, gases, or mixtures thereof that also include solid particles in a fluid carrier. Liquids may include mixtures of two or more different liquids, solutions, slurries, or suspensions.

Fluids may include components such as, for example, cells, cellular fractions or components, collections or aggregations of cells, bacterial, viral or fungal species, ions, molecules, gas bubbles, dissolved gas, suspended particles, or a variety of other materials that may be present in the body of a mammal. Fluid components may be materials that are normally present in the body fluid of an organism (e.g., a mammal), materials that are naturally derived but not normally present in the body fluid, or foreign materials that have entered or been introduced to the body fluid (including but not limited to pathogens, toxins, pollutants, or medications, for example).

Examples of liquids present within body lumens include blood, lymph, serum, urine, semen, digestive fluids, tears, saliva, mucous, cerebro-spinal fluid, intestinal contents, bile, epithelial exudate, or esophageal contents. Liquids present within body lumens may include synthetic or introduced liquids, such as blood substitutes, or drug, nutrient, or saline solutions. Fluids may include liquids containing dissolved gases or gas bubbles, or gases containing fine liquid droplets or solid particles. Gases or gaseous mixtures found within body lumens may include inhaled and exhaled air, e.g. in the nasal or respiratory tract, or intestinal gases.

The system of the present embodiments is particularly useful for use with fluids characterized by Reynolds number which is less than 1 or less than 0.9 or less than 0.8 or less than 0.7 or less than 0.6 or less than 0.5 or less than 0.4 less than 0.3 or less than 0.2 or less than 0.1. Such a low Reynolds number is characteristic in small scale environments and in viscous fluids.

When system 50 is embodied as a self-propelled vehicle, it is adapted to the environment in which the vehicle is intended to move.

System 50 is useful in medical applications for self-propulsion of a catheter or an endoscope through a lumen, by its tip. It can be applied in various medical fields such as Endoscopy, Gastro-entereology, Urology, Cardiology, Cochlear implantation, joints surgery, sub-dural spinal applications, and others.

In some embodiments of the present invention the vehicle is adapted for being introduced into (e.g., configured to fit within) a body lumen of an organism (e.g., a mammal). The dimensions of system 50 in these embodiments are from about 1 mm to about 15 mm in diameter, and from about 5 mm to about 150 mm in length.

Representative examples of body lumens into which system 50 can be introduced include, without limitation, the respiratory tract, the cardiovascular system (e.g., a blood vessel, either an artery or a vein), a portion of a CSF-space (cerebro-spinal fluid space) of the nervous system (e.g., the spinal canal, the ventricles of the brain, the sub-arachnoid space, etc.), a portion of the urinary tract (for example a ureter), a portion of the lymphatic system, a portion of the abdominal cavity, a portion of the thoracic cavity, a portion of the digestive tract, a portion of a reproductive tract, either the female reproductive tract (e.g., a lumen of a fallopian tube) or the male reproductive tract (including various lumens including but not limited to the epididymis, vas deferens or ductal deferens, efferent duct, ampulla, seminal duct, ejaculatory duct, or urethra), the biliary tract, a nostril or nasal cavity, the oral cavity, the digestive tract, the tear ducts, or a glandular system. Other body lumens may be found in the auditory or visual system, or in interconnections thereof, e.g., the Eustachian tubes. In some embodiments of the present invention system 50 is used in body lumens through which fluid (e.g., liquid) flows, but it is not intended that such devices or systems are limited to use in structures containing moving fluid. In some applications, system 50 is used in a body lumen containing relatively unmoving, or intermittently moving fluid (liquid), or partially filled with liquid.

Also included within the scope of the term "body lumen" are man-made lumens within the body, including vascular catheters, spinal fluid shunts, vascular grafts, bowel re-anastomoses, bypass grafts, indwelling stents of various types (e.g., vascular, gastrointestinal, tracheal, respiratory, ureteral, genitourinary, etc.) and surgically created fistulas.

System 50 is also applicable to non-medical applications, for example, where vision, accessibility or maintenance are needed in passageways. Thus, in some embodiments of the present invention the vehicle is adapted for being introduced into a non-biological medium such as, but not limited to, a pipe, a channel, a building duct, a borehole, a pool and soil. The dimensions of system 50 in these embodiments can be are from about 1 mm to about 500 mm in diameter, and from about 5 mm to about 5000 mm in length.

System 50 can be used for displacing (e.g., delivering to a site) various types of objects. This embodiment is useful particularly, but not exclusively, when system 50 is introduced into a body lumen as a self-propelled vehicle. Each object to be delivered can be encapsulated in one of casings 52 and 54. Representative examples of objects that can be encapsulated and delivered including, without limitation, a drug, a camera, a distal end of an endoscope, a sensor, a stent, and an electrical and/or magnetic stimulation device. System 50 may optionally and preferably comprise an object release structure configured to release the object, for example, in response to receipt of a signal by communication device 62.

In some embodiments of the present invention system 50 is introduced into a liquid medium having a viscosity of at least 1 cSt when the smallest dimension of the system is at the millimeter scale (e.g., from about 1 mm to about 1 cm), and at least 1,000 cSt or at least 10,000 cSt or at least 100,000 cSt or at least 1,000,000 cSt when the smallest dimension of the system is at the centimeter-meter scale (e.g., from about 1 cm to about 10 meters).

Representative examples of liquid media suitable for the present embodiments include silicon fluid, detergent product, putties and caulking compounds, sludge, sputum, pus, pleural fluid, gastric aspirate, endotracheal aspirate, transtracheal aspirate, bronchoalveolar lavage, laryngeal swab, and nasopharyngeal swabs. Also contemplates are liquid food products such as, but not limited to, honey, cheeses, lards and shortenings, ground meat, sugars, and doughs.

When the system of the present embodiments is employed as a pump, it can be used for pumping and optionally dispensing many types of fluids. In these embodiments, the system is fixated with a lumen containing the liquid medium to be pumped, and a rotary motion of the camshaft is established. Due to the fixation of the system, the generated traveling wave in the shell provides the pumping functionality. The system of the present embodiments has many advantages over conventional pumps.

One advantage is the ability of the system of the present embodiments to operate in lumens having rigid walls. This is advantage over, for example, peristaltic pump, which can only operate in lumens having flexible and elastic walls. Thus, in some embodiments of the present invention the system is introduced into a lumen having walls characterized by a modulus of elasticity of at least 10 GPa, or at least 100 GPa or at least 200 GPa.

Another advantage is the ability of the system of the present embodiments to generate locomotion of liquid material at low shear rate and with no physical contact between pumping elements, or between pumping elements and pump walls. Shear forces may result in excessive shear strain in the material that can change the character of the liquid, break large molecules, or harm transported cells or particles. This is particularly advantageous in the water treatment, polymer, paper and coatings industries. This excessive shear strain may also be characterized as excessive "working" of the material such that the material may lose its desired characteristics or integrity. For example, in the fields of life science and medicine, centrifugal pumps have been conventionally used in order to achieve relatively large flow rates of blood to and from the patient's body. Although the centrifugal pumps can achieve the necessary high flow rates, the centrifugal pumps create relatively large shear forces on the blood resulting in an undesirable amount of hemolysis. Hemolysis is a particular concern with heated blood, since the membranes of the red blood cells are weaker at higher temperatures, and thus the cells are much more prone to rupturing when subjected to shear forces at high temperatures. In the food industry, fatty meat is sensitive to the imposition of shear forces, since it contains a significant quantity of fat, wherein excessive shear forces and resulting strain result in an undesired appearance of fat over the exposed surfaces. In various exemplary embodiments of the invention the system generate locomotion of liquid material at shear rate less than $10 \, s^{-1}$, e.g., from about $0.1 \, s^{-1}$ to about $10 \, s^{-1}$, or from about $0.1 \, s^{-1}$ to about $6 \, s^{-1}$, or from about $0.2 \, s^{-1}$ to about $4 \, s^{-1}$.

An additional advantage of the system of the present embodiments is the ability to pump liquid of high viscosity. Traditional centrifugal pumps have problems with cavitation, clogging, binding, and high wear when used with highly viscous liquids. This is due to the intrinsic nature of a typical centrifugal pump in which the impeller has vanes which are designed to shear and sling a liquid in order to impart a centrifugal force thereon. Use of specially designed impellers, is also problematic since this solution is highly inefficient due to considerable slippage and dead zones.

Another advantage of the system, contrary to most peristaltic pumps is the ability to pump fluids at approximately constant flow rate, rather than pulsating bursts of fluid.

Following is a more detailed description of the dynamics of system 10, according to some embodiments of the present invention. A nomenclature including the symbols used in the following description is provided in Appendix 1, below.

Since the cams are rotating, any given cam profile exerts a periodic torque on the shaft. Without lose of generality, harmonic cams are considered in the following description. Since a periodic function can be decomposed into a sum of harmonic components (Fourier expansion) the analysis of harmonic cams is applicable for any general cam profile designed to produce a general wave profile.

FIG. 4 illustrates a cam profile and a corresponding pitch profile generated during the rotation of the cam. For a single-harmonic cam profile, the following form of a pitch curve is assumed $$r_p = r_0 + a \cos(N\theta). \tag{1}$$

For a multi-harmonic cam profile, the following form of a pitch curve is assumed $$r_p = r_0 + \sum_{n=1}^{N_H} b_n \cos(nN\theta) \tag{1a}$$

where $N_H$ is the number of harmonics in the cam profile.

The following description primarily relates to the case of a single-harmonic cam profile. The case of multi-harmonic cam profile is described in the Examples section that follows (see Example 3).

The force exerted by a single roller follower on a cam, assuming no cam to follower disengagements, is given by [29]:

$$F(\theta) = \frac{f_k(\theta) + m_f \ddot{r}_p(\theta)}{\cos\alpha(\theta) - \mu\left(\frac{2(A - a\cos(N\theta)) + B}{B}\right)\sin\alpha(\theta)}, \tag{2}$$

where the pressure angle is given by $$\alpha(\theta) = \tan^{-1}\left(-\frac{\frac{\partial r_p}{\partial \theta}}{r_p}\right). \quad (3)$$

In EQ. (2), the effect of viscous damping has been neglected. It was found by the present inventors that the system of the present embodiments can operate efficiently both when the viscous damping is negligible and when the viscous damping is non-negligible. The former case is described below. The latter case is described in the Examples section that follows (see Example 3).

Neglecting shell flexural rigidity comparing with membranous effects [30], and assuming axial symmetry and small deflections, the radial shell stiffness can be considered as linear and given by:

$$\kappa = \frac{K\hat{h}S}{(d_0/2)^2} \quad (4)$$

The elastic radial force exerted by the cylindrical membrane is now given by:

$$f_k = \kappa\left(r_p + h - \frac{d_0}{2}\right) \quad (5)$$

Thus, the torque exerted by an arrangement of N cyclic-symmetrical cam followers is given by:

$$T(\theta) = \frac{BaN^2}{4}\begin{pmatrix} \left(\begin{array}{c}(m_fN^2\omega^2-\kappa)a^2+\\2(d_0-2(r_0+h))r_0\kappa\end{array}\right)\sin(N\theta) + \\ \left(\begin{array}{c}2m_fN^2\omega^2 r_0+\\(d_0-2h-4r_0)\kappa\end{array}\right)a\sin(2N\theta) + \\ (+m_fN^2\omega^2-\kappa)a^2\sin(3N\theta) \\ \left(\mu Na((2A+B)\sin(N\theta)-a\sin(2N\theta))-\right) \\ B(r_0+a\cos(N\theta)) \end{pmatrix} \quad (6)$$

The resultant torque on the shaft is then given by:

$$T_t(\theta) = \sum_{n=1}^{N_c} T(\theta + (n-1)\Delta\theta), \quad (7)$$

where $\Delta\theta = 2\pi M/(N \cdot N_c)$ as further detailed hereinabove. Since the torque on each cam is periodic (6), it can be expanded in a Fourier series $$T(\theta) = a_0 + \sum_{k=1}^{\infty} a_k\sin(k\theta) + b_k\cos(k\theta), \quad (8)$$

where $a_k$ and $b_k$ are constants that depend of the geometrical and physical parameters N, M, $\mu$, $r_0$, d etc. Note that for $\mu=0$, EQ. (6) is an odd function of $\theta$ and the series is comprised only of sine terms. Substituting EQ. (8) into EQ. (7) yields:

$$T_t(\theta) = N_c\alpha_0 + \sum_{n=1}^{N_c}\sum_{k=1}^{\infty}\sin\left(\begin{array}{c}a_k\sin\left(k\left(\theta+(n-1)\frac{2\pi M}{N_c}\right)\right)+\\b_k\cos\left(k\left(\theta+(n-1)\frac{2\pi M}{N_c}\right)\right)\end{array}\right), \quad (9)$$

which can also be written as:

$$T_t(\theta) = N_c a_0 + \sum_{n=1}^{N_c}\sum_{k=1}^{\infty} c_k \sin\left(\varphi_k(\theta) + (n-1)\frac{2\pi k M}{N_c}\right). \quad (10)$$

EQ. (10) can also be written as:

$$T_t(\theta) = N_c a_0 + \sum_{k=1}^{\infty} c_k \sum_{n=1}^{N_c}\sin\left(\varphi_k(\theta) + (n-1)\frac{2\pi k M}{N_c}\right). \quad (11)$$

By integration it can be shown that for $\mu=0$, $a_0=0$ corresponding to zero mean torque.

It was proven by the present inventors that the sums $$\sum_{n=1}^{N_c}\sin(\varphi_k(\theta) + (n-1)2\pi k M/N_c) \quad (12)$$

all equal zero individually for every k, provided that, $N_c$ and k·M are integers, and $kM/N_c$ is non-integer, for all values of k=1, 2, 3, . . . K, and where K is the highest harmonic of finite magnitude in the sum (9).

For $\mu\neq 0$, $a_0\neq 0$ the mean total torque is not identically zero, because the elastic restoring force cannot eliminate the non-restoring friction force. Nevertheless, it was found by the present inventors that the amplitude of torque oscillations approaches to zero by eliminating the harmonic sums (12) provided that $N_c$ and k·M are integers, and $kM/N_c$ is non-integer.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which, for brevity, are described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Computer Simulations

It was found by the present inventors that the system can be optimized so as to find a suitable number of cams and wavelengths, given a specific value for the friction coefficient. An optimal torque can be defined as satisfying a condition of minimal mean squared torque integrated over one shaft revolution (RMS or signal energy):

$$\min_{M, N_C} J = \sqrt{\frac{1}{2\pi} \int_0^{2\pi} T_t^2(\theta) d\theta} . \quad (13)$$

This definition accounts for both mean magnitude and oscillations amplitude. It leads to minimal power consumed by the driving motor for a constant speed of rotation. Since the harmonics are orthogonal, each of the harmonics in the signal in (13) before the root is taken is weighed by its amplitude squared (including the mean).

Numerical simulations of the cost function J for arbitrary geometrical and physical constants are shown in FIGS. 5A-B assuming negligible (FIG. 5A) and non-negligible (FIG. 5B) friction for $N_c/M > 2$. The minima in the vicinity of integer wavelengths M are clearly identified. In FIGS. 5A-B, the colors represent torque magnitude in Nm (color bar in FIG. 5A).

The effect of introducing a deliberate error from the optimal value of the phase shift between the cams, on the torque on individual cams and on the resultant shaft torque is demonstrated in FIG. 6A-D for negligible friction and in FIGS. 7A-D for non-negligible friction. As shown in FIGS. 6A-D, by choosing an appropriate phase shift between the cams, the torque on each cam is unaltered, however the resultant torque is zero (purple line FIG. 6A for negligible follower inertia and 6C for non-negligible follower inertia), while a slight deviation of only 2 degrees (less than 7% relative error) from the correct phase angle between two subsequent cams, results in torque oscillations (purple line in FIG. 6B for negligible follower inertia and 6D for non-negligible follower inertia). Similar results were obtained for both negligible and non-negligible follower inertia.

Figure 7A:
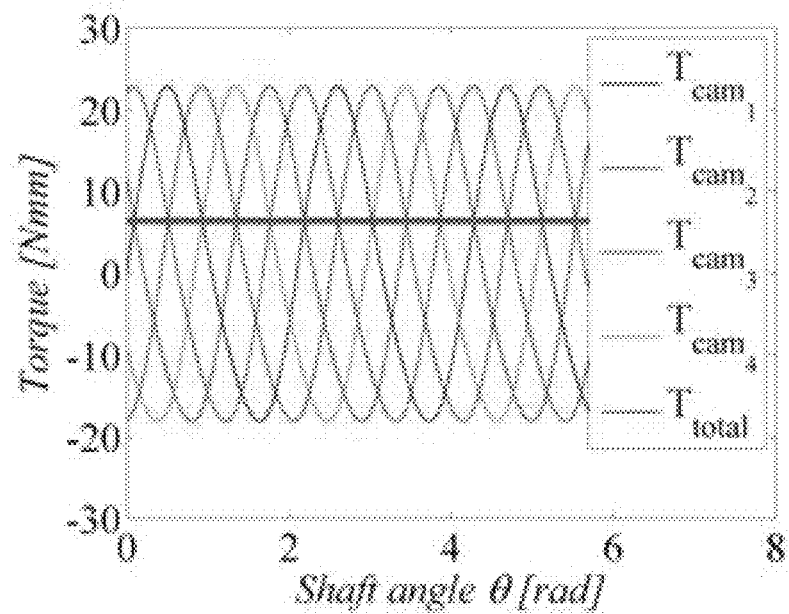
Figure 7B:
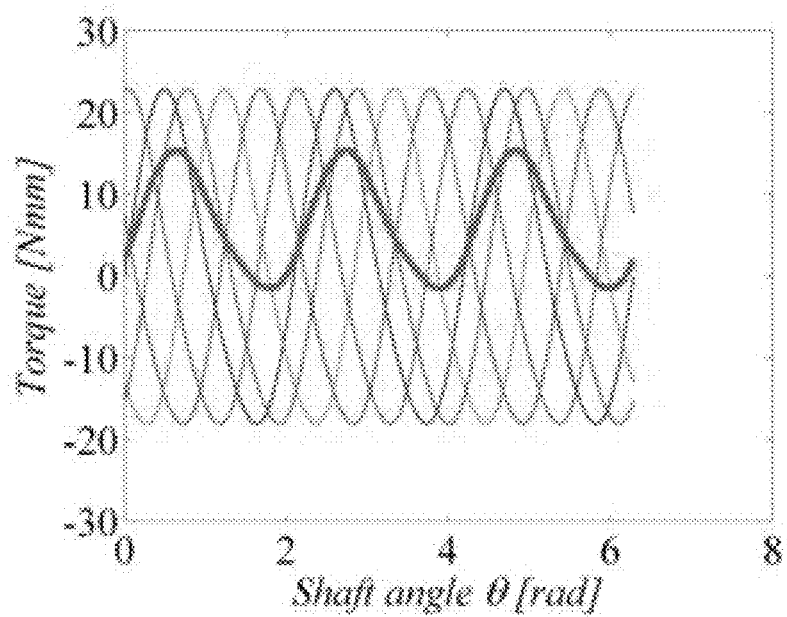
Figure 7C:
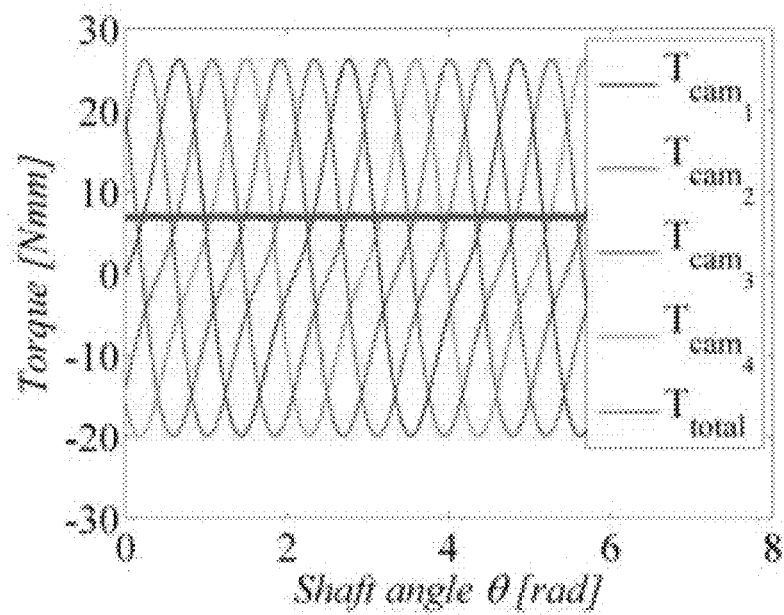
Figure 7D:
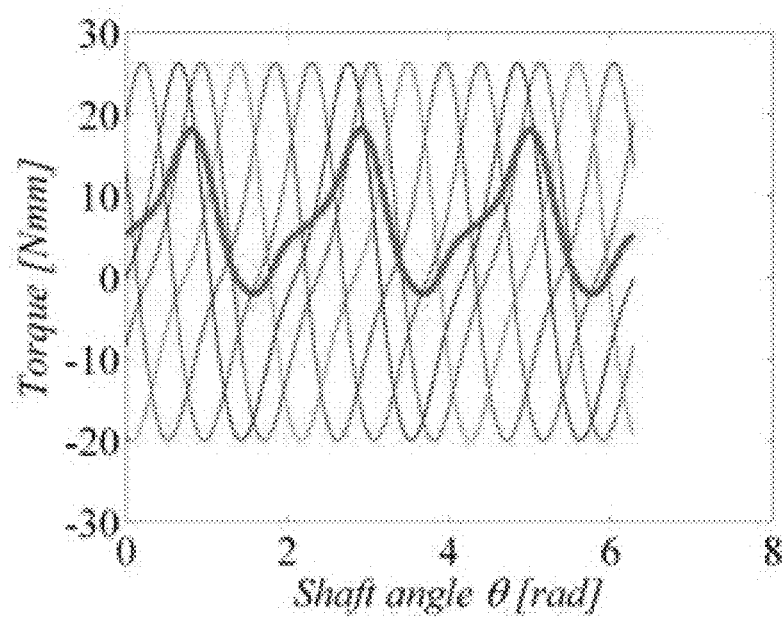

In FIGS. 7A and 7C the appropriate phase shift results in a constant torque with attenuated oscillations. The result of introducing a deliberate phase error of 2 degrees is depicted in FIGS. 7B and 7D for negligible and non-negligible follower inertia respectively where significant torque oscillations are present.

Figure 8A:
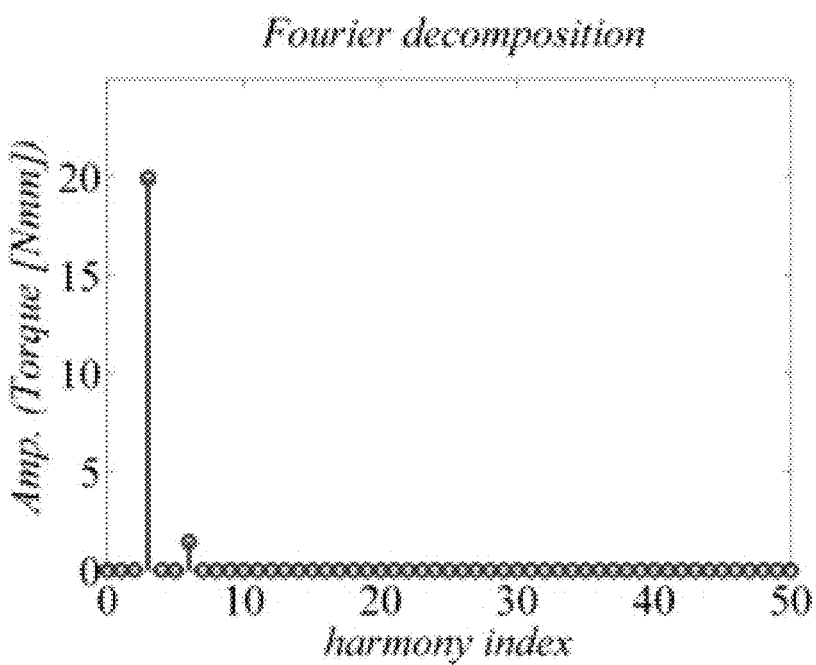
Figure 8B:
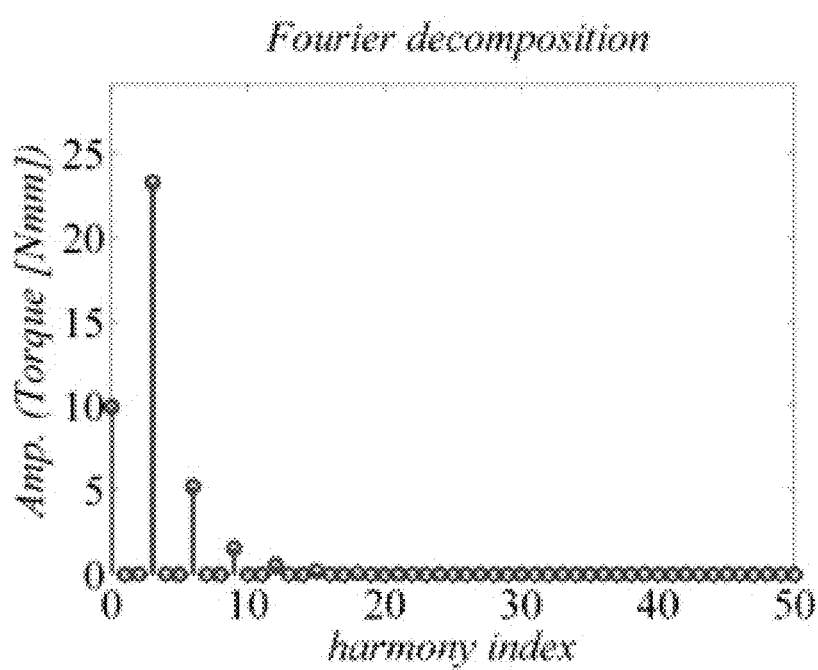
Figure 8C:
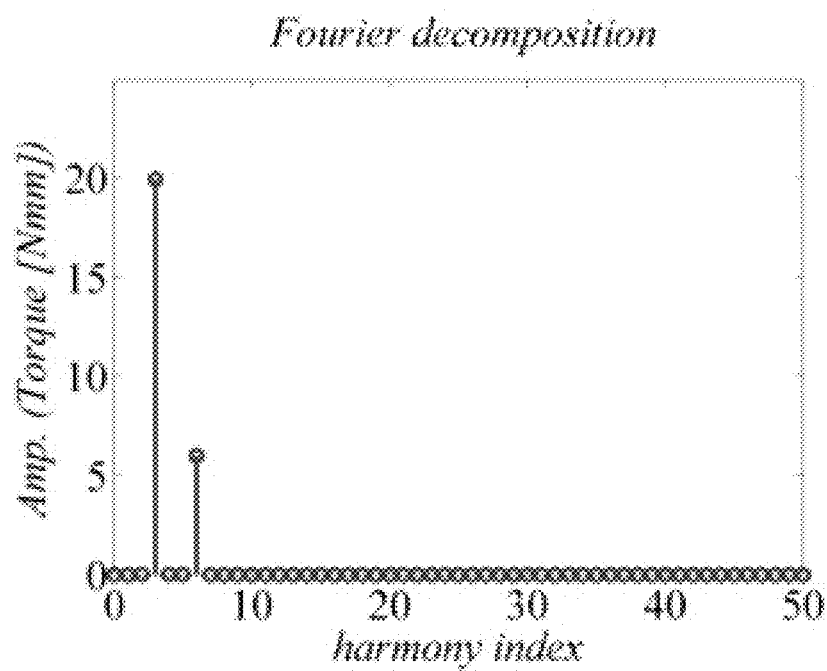
Figure 8D:
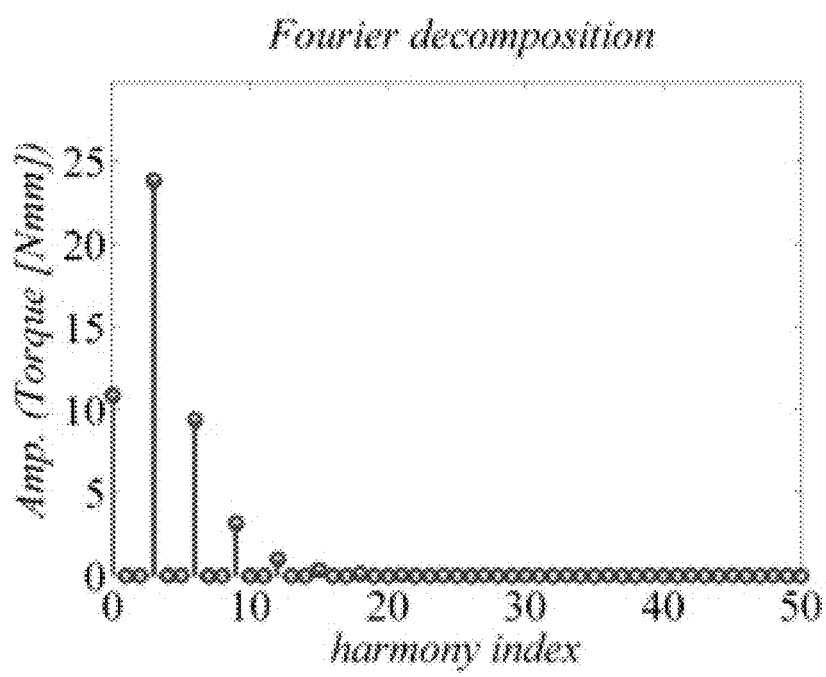

The effect of non-negligible inertia is also demonstrated in FIGS. 8A-D, where the frequency decomposition of the torque exerted on a single cam is presented. Shown is a discrete Fourier decomposition (FFT) of the periodic torque exerted on a single cam for arbitrary geometrical parameters. FIG. 8A shows simulation results for the case of negligible friction and negligible inertia ($\mu=m_f=0$), FIG. 8B shows simulation results for non-negligible friction and negligible inertia ($\mu=0.5$, $m_f=0$), FIG. 8C shows simulation results for negligible friction and non-negligible inertia ($\mu=0$, $m_f=5$ gr), and FIG. 8D shows simulation results for non-negligible friction and non-negligible inertia ($\mu=0.5$, $m_f=5$ gr). All plots are for N=3.

While the introduction of friction results in added harmonics in the frequency content of the torque signal (FIGS. 8B and 8D, vs. FIGS. 8A and 8C respectively), the introduction of inertia does not change the frequencies, but rather changes the magnitude of the frequency coefficients (FIGS. 8C and 8D vs. FIGS. 8A and 8B respectively). This result can also be deducted from the analytical expression given in EQ. (6), where the inclusion of the inertial term $m_f N^2 \omega^2$ affects only the magnitude of the coefficients of the harmonic expressions. The outcome of this conclusion is that inclusion of follower inertia does not change the number of cams required to eliminate torque oscillations, whereas inclusion of friction does.

Additional computer simulations were conducted to study the vorticity field generated by the system of the present embodiments during its operation in fluid. A computer simulated model of a pump system, according to some embodiments of the present invention is illustrated in FIGS. 9A-B. The system is immersed in quiescent fluid. Computer simulation results of the vorticity field $\omega_\theta = \partial v_r/\partial z - \partial v_z/\partial z$ generated by the system are shown in FIG. 10. Shown are an axi-symmetrical normalized vorticity field (color coded), and velocity vector direction (arrows), generated by the system (wave propagating downwards).

As shown, the vorticity field along the shell, consists of alternating vortices of opposite signs. The more dominant toroidal vortices, both in absolute magnitude and in spatial distribution, are the negative (blue-colored in FIG. 10), which induce net flow field in the direction of the wave propagation (negative z axis), which in turn yields stresses in the opposite direction, resulting in thrust in the direction of the direction of propagation of the free swimmer system (positive z axis).

Example 2

Experimental Study

A prototype of an autonomous robotic swimmer system was designed and fabricated, according to some embodiments of the present invention. The swimmer system utilized an approximately axi-symmetric surface, transverse traveling waves. The waves were generated by the mechanism as detailed hereinabove. The system was similar to system 50 (FIG. 3) and included a mechanical and an electronic sections encapsulated in casing 52, a wave generating system 10, and a power section encapsulated in section 54. The mechanical section incorporated a DC motor coupled to the wave generating system 10, an electronics section included a microcontroller, sensors, communication and voltage regulation units, and the power section with a set of rechargeable batteries and charging circuit. The dimensions of the prototype system were 50 cm in length, and 30 mm in radius.

The prototype system was composed of polypropylene casings, commercial Perspex (PMMA) semispherical caps were bolted to the cylinders and sealed by flat gaskets. The camshaft was made of PMMA and included $N_c$=32 cams, and N=3 roller-cam-followers for each cam, made from aluminum and stainless-steel bearings. The shell was embodied as a liquid-proof elastic cylindrical membrane (natural latex of width of about 0.05 mm), which also performs as a retaining spring for the cam-followers. The prototype swimmer system was equipped with metal weights to maintain levelness and sufficient buoyancy when immersed in silicone fluid. The camshaft was rotated by a DC motor and an Oldham coupling. The motor was powered by a set of rechargeable batteries (11.1V, 2600 mA/hr) via PWM (pulse width modulation) signal. PWM signal generation, control and communication were managed by a microcontroller (8 bit, PIC18F1330), a set of sensors, and interfacing electronic circuit.

The experimental setup is illustrated in FIG. 11. The setup included a tank containing silicone fluid (dynamic viscosity $\mu$=58.6 Pa s, density $\rho$=967 kg/m$^3$), in which the prototype system was immersed. Since the silicone oil is dielectric, wireless communication between a PC and an onboard microprocessor was employed using Bluetooth®. The speed of the prototype system was controlled by a remote PC, which also receives the orientation using a tri-axis accelerometer, and motor rpm using microcontroller timer and Hall-effect encoder. The position of the prototype system was traced by a video camera and image processing tools.

Results

Representation of the actual waving envelope was obtained by moderately fast image acquisition system (60 fps) of the waving motion. The captured images undergo an envelope edge analysis (edge detection). A representative captured image is shown in FIG. 12A. The tempo-spatial envelope of the waving section is shown in FIG. 12B. Traveling waves of primary wavelength $\lambda$=20 mm were observed.

The velocity of the prototype system was recorded for several wavelengths ($\lambda$=20, 30 and 40 mm), in a range of wave velocities. The wavelength was controlled by setting the angular spacing between the cams. The results are shown in FIG. 13. The measured data are shown with ±3σ variance limits, and dashed fitted smooth curves. As shown, the swimming speed increases with wave velocity, and decreases with wavelength.

Example 3

Additional Considerations

In Example 1, a pitch profile consisting of a single angular wavenumber was considered. This embodiment is useful for generating a traveling wave of a single wavelength.

In the present Example, a multi-harmonic cam profile comprising a sum of harmonic components is considered. This embodiment is useful for generating a complex traveling wave. This profile can be represented by a Fourier series in terms of the spatial harmonics. EQ. 1B above describes a multi-harmonic pitch profile expressed in polar coordinates, and is rewritten below as EQ. 14:

$$r_p = r_0 + \sum_{n=1}^{N_H} b_n \cos(n N \theta). \tag{14}$$

$N_H$ is the number of harmonics in the pitch profile and $b_n$ (n=1, 2, ..., $N_H$) is the amplitude of the nth harmonic. It is assumed that the cam-followers are of the roller type and the cam profile is selected to yield the desired pitch profile while compensating for the roller radius.

FIG. 14 shows the forces acting on a cam follower (red): a normal force due to cam contact F, normal forces due to linear bearing $N_1$, $N_2$, distributed elastic restoring forces due to cylindrical shell $f_k$, and a general dissipative force f (roller follower rising).

Linear momentum balance on a cam follower results in the force exerted by a single roller follower on a cam, assuming a thin follower (direction of dry friction force is embedded in the sign of the sine term):

$$F = \frac{f_k + c\dot{r}_p + m_f \ddot{r}_p}{\cos\alpha - \mu\left(\frac{2A+B}{B}\right)\sin\alpha}, \tag{15}$$

where c is the viscous damping coefficient, $\mu$ is Coulomb friction coefficient, $f_k$ is an elastic restoring force, $\alpha$ is the pressure angle, B is the length of the follower linear bearing, and A is the roller follower overhang (see FIGS. 4 and 14).

Neglecting shell flexural rigidity compared with membranic effects and assuming axial symmetry and small deflections of the elastic cylindrical shell, it can be shown that the radial restoring force is linear and the radial stiffness is given by $$k_S = E\hat{h}S / \left(\frac{d_0}{2}\right) \quad (16)$$

where E is the elasticity modulus, ĥ is the shell thickness, S is the surface fraction covered by an arched beam, and $d_0$ is the undeformed diameter of the shell. The elastic radial restoring force exerted by the cylindrical shell is now given by $$f_k = k_S \left(r_p + h - \frac{d_0}{2}\right) \quad (17)$$

where h is the follower length. It is assumed at all times that the elastic cylindrical shell maintains positive tension and provides enough restoring force to prevent cam-follower disengagements. The cam follower overhang is given by $$A = A_0 - (r_p - r_0), \quad (18)$$

where $A_0$ is the mean overhang. The pressure angle, the angle between the normal to the pitch curve and the follower velocity vector is given by (with zero followers offset):

$$\alpha = \tan^{-1}\left(\frac{1}{r_p}\frac{dr_p}{d\theta}\right), \quad (19)$$

(positive pressure angle where the follower is ascending, i.e., $dr_p/d\theta > 0$).

The torque exerted by a single cam-follower on a single cam is given by $$T = r_p F \sin \alpha. \quad (20)$$

Substituting EQs. (15)-(19) into EQ. (20) while exploiting cyclic symmetry of the design yields the torque exerted by N circumferential cam-followers on a single cam $$T = \frac{N\left[k_S\left(r_p + h - \frac{d_0}{2}\right) + cr_p' + m_f \ddot{r}_p\right] r_p r_p' B}{r_p B - \mu[2(A_0 - r_p + r_0) + B] r_p'}, \quad (20)$$

where r' denotes derivative with respect to θ.

Following is a harmonic analysis of the torque. Denote:

$$T = a_0 + \sum_{k=1}^{\infty} a_k \sin(kN\theta + \varphi_k), \quad (22)$$

where $a_0$ is the mean torque on a cam, $a_k$ and $\varphi_k$ are the amplitude and phase of the kth harmonic, respectively, in the torque signal.

According to EQ. (21), when the Coulomb friction is negligible, the torque on a cam is a linear combination of the terms $r_p'$, $r_p r_p'$, $\ddot{r}_p r_p'$ and $\ddot{r}_p r_p'$. Assuming constant angular velocity (Ω) and relying on Eq. (14), the spatial (angular) frequencies of the torque contains energy at discrete, equally spaced spectral lines with respect to the rotation angle θ and are given by {(n±m)N}; n, m=0, 1, . . . , $N_H$. The non-zero means (DC) is contributed only by the term $\dot{r}_p r_p'$, which is preceded by the viscous damping coefficient. By averaging Eq. (21) over a period it can be shown that the mean torque on a single cam for negligible dry friction and non-negligible viscous damping, due to circumferential cam-followers is given by $$\langle T \rangle|_{\substack{\mu=0 \\ c \neq 0}} = \frac{1}{2} c N^3 \Omega \sum_{n=1}^{N_H} n^2 a_n^2. \quad (23)$$

By assuming a pitch-profile of a single harmonic ($N_H = 1$) with a small amplitude $a_1$, expanding Eq. (21) in power series of the pitch radius amplitude $a_1$, and averaging over a period, it can be shown that the mean torque on a single cam is given by a series of even powers of the amplitude $a_1$. Even powers are expected since the mean non-zero torque due to friction cannot be affected by the mathematical sign of the amplitude, which is equivalent to shaft rotation. The leading order term of the mean torque (assuming small amplitude) is then given by $$\langle T \rangle|_{\substack{\mu=0 \\ c \neq 0 \\ a_1 \ll 1}} = \mu a_1^2 \frac{N^3 k_S}{2Br_0}(2A_0 + B)\left(r_0 + h - \frac{d_0}{2}\right) + \frac{1}{2} c a_1^2 N^3 \Omega. \quad (24)$$

The expression given in Eq. (24) is a sum of positive components, where $r_0 + h - d_0/2 > 0$ as it represents the mean radial displacement of the elastic cylindrical shell, which is assumed to maintain positive tension all times. When the expressions in Eqs. (23)-(24) are multiplied by the number of cams, they represent the optimal (minimal) resultant shaft torque in the presence of viscous damping and dry friction, respectively, where torque oscillations have been eliminated.

Thus, when both Coulomb friction and viscous damping are negligible, the torque on each cam oscillates with zero mean, and when Coulomb friction is significant, it's non-linear contribution further increases the number of harmonics composing the periodic torque (Eq. (22)). The number of harmonics comprising the periodic torque on a single cam therefore depends on the number of wavelengths in the desired wave $N_H$ and the magnitude of the dry friction μ.

The resultant torque on the camshaft from summing up the torques on each cam can be written as $$T_t = \sum_{n=1}^{N_c} T(\theta) \bigg|_{\theta = \theta + (n-1)\Delta\theta} \quad (25)$$

Substituting Eq. (22) into Eq. (25) yields after some manipulations $$T_t = N_C a_0 + \Im\left[\sum_{k=1}^{\infty} a_k e^{i(\varphi_k + kN\theta)} \sum_{n=1}^{N_c} r^{n-1}\right], \quad r \triangleq e^{i\frac{2\pi km}{N_c}} \quad (25)$$

where the operator $\Im$ extracts the imaginary part of a complex number. The last representation is convenient in determining the optimal set of parameters that minimizes the torque oscillations, according to some embodiments of the present invention.

The present inventors have proven that the residual oscillating terms in the complex series in EQ. (26) equal zero individually for every k, provided that kM is an integer number and $kM/N_c$ is a non-integer for k=1, 2, . . . , K, where K is the highest harmonic of finite magnitude in EQ. (22).

FIGS. 15A-B show torque load curves on successive cams $T_1$, . . . , $T_4$ and resultant torque $T_t$ on the shaft as a function of the rotation angle for inaccurate phase shift (FIG. 15A) where 1° error is deliberately introduced and correct phase shift $\Delta\theta=30°$ (FIG. 15B). The curves were calculated numerically assuming negligible dissipative losses ($\mu=c=0$, N=3, $N_c=4$, M=1).

FIGS. 16A-B show torque load curves on successive cams $T_1$, . . . , $T_4$ and resultant torque $T_t$ on the shaft as a function of the rotation angle for inaccurate phase shift (FIG. 16A) where 1° error is deliberately introduced and correct phase shift $\Delta\theta=30°$ (FIG. 16B). The curves were calculated assuming minor viscous damping that yields non-zero constant optimal resultant torque ($\mu=0$, c=0.1, N=3, $N_c=4$, M=1).

As shown in FIG. 15A, a slight deviation of one degree from the optimal relative angular rotation shift causes considerable resultant torque oscillations (purple pluses in FIG. 15A). Selecting the optimal phase shift between the cams results in zero resultant shaft torque $T_t$, as demonstrated in FIG. 15B.

When viscous damping is introduced (FIGS. 16A-B), the non-optimal phase shift (phase error of one degree) results in significant total torque oscillations. An optimal relative phase can be produced that yields a non-zero constant torque with considerably low or no torque oscillations. The mean torque is not eliminated completely since dissipation is not conservative and is not nullified by elastic forces. The magnitudes of the mean resultant shaft torque for viscous damping and for dry friction were successfully compared with the analytical expressions in EQs. (23)-(24).

FIG. 17A shows RMS of shaft torque [Eq. (13)] plotted as a function of the number of cams and number of wavelengths in the shell, for $\mu=0$, c=0.5 Ns/mm, N=3, $N_H=1$, $N_c>2$ and $N_c/M>2$.

FIG. 17B shows Harmonic decomposition of the spatial (angular) frequencies of the torque load on a single cam for $\mu=0$, c=0.5 Ns/mm, N=3, $N_H=1$.

As shown FIG. 17A, when viscous damping is not negligible (c=0.5 Ns/mm), the optimal shaft torque RMS (minima area) is non-zero and increases with the number of cams, as predicted by Eq. (26). In FIG. 17B a non-zero component is present in the spatial frequency content. In FIG. 17A, the colors represent torque magnitude in Nm (see color bar).

According to EQ. (21), dry friction or a multi-harmonic cam-profile give rise to higher harmonics in the cam torque signal.

FIG. 18A shows RMS of shaft torque [Eq. (13)] plotted as a function of the number of cams and number of wavelengths in the shell for $\mu=0.8$, N=3, $N_H=7$, $N_c>2$ and $N_c/M>2$. In FIG. 18A, the colors represent torque magnitude in Nm (see color bar).

FIG. 18B shows Harmonic decomposition of the spatial (angular) frequencies of the torque on a single cam for $\mu=0.8$, N=3, $N_H=7$.

As shown in FIGS. 18A-B, higher harmonics are present, leading to non-trivial combinations for which $kM/N_c$ is an integer, thus violating the conditions that kM is integer and $kM/N_c$ is non-integer. RMS magnitudes were observed along the lines where $kM/N_c$ is an integer (FIG. 18A).

The above Examples demonstrated that the system of the present embodiments is capable of producing three-dimensional traveling waves of many types. Specifically, the above Examples demonstrated that the system of the present embodiments can generate both a single-harmonic three-dimensional traveling wave, as well as a complex three-dimensional traveling wave, and that the single-harmonic or complex three-dimensional traveling wave is generated when Coulomb friction is either negligible or non-negligible, and when the viscous damping is either negligible or non-negligible, in any combination.

APPENDIX 1

Nomenclature

N—No. of angular wavelengths per cam
L—axial length of waving mechanism
$\hat{h}$—shell thickness
z—axial coordinate
r—radial coordinate
θ—azimuthal coordinate
$r_0$—mean radius of cam pitch profile
$r_p$—cam pitch profile
a—cam pitch profile amplitude
$\hat{r}_0$—radial midsurface of the system, interchangeably denoted $r_m$
$\hat{r}_1$—radial wetted surface of the system
U—wave velocity of the system
$\hat{V}$—swimming velocity of the system
λ—wavelength of the system
$\hat{b}$—wave amplitude of the system, interchangeably denoted a
$\hat{a}$—undeformed midsurface radius of the system, interchangeably denoted $d_0/2$
M—No. of axial wavelengths
$N_c$—No. of cams
k—an integer index of the harmonics comprising the periodic signal of torque on a single cam
K—a predetermined parameter, typically representing the highest index in a Fourier expansion of the torque on a single cam for which the respective harmonic has a magnitude which is higher than 5% of the mean torque.
E—Young's modulus of shell wall
S—cam follower—shell contact surface
Δθ—angular phase between successive cams
F(θ)—follower—cam normal force
T(θ)—Torque on cam
$T_t(\theta)$—total torque on shaft
A—mean cam follower overhang
B—cam follower linear bearing length
a(θ)—cam pressure angle
μ—cam follower coefficient of friction
h—cam follower height
ω—camshaft angular velocity
a—pitch profile amplitude
$d_0$—shell undeformed diameter
$m_f$—cam follower mass
$f_k$—retaining spring force on a cam follower
κ—radial stiffness of elastic cylindrical membrane
$a_0$—mean value of the periodic torque on a single cam
$a_k$, $b_k$—the coefficients of the sine and cosine terms of the k'th harmonic comprising the periodic torque on a single cam
$c_k$—the magnitude of the kth harmonic comprising the periodic torque on a single cam
$\varphi_k(\theta)$—harmonic dependent phase in torque sum
J—optimization cost function, torque on shaft root mean squared
$v_r$—radial velocity component of fluid particle $v_z$—axial velocity component of fluid particle
$\omega_\theta$—fluid vorticity magnitude
$\sigma$—standard deviation
$N_1, N_2$—normal forces acting on cam-follower in a certain embodiment of the system
$N_H$—number of spatial harmonics in a multi-harmonic cam profile
$b_n$—the amplitude of the nth harmonic in a multi-harmonic cam profile
f—any dissipative force acting on a cam follower in a certain embodiment of the system
$k_s$—radial stiffness of elastic cylindrical membrane
c—viscous damping coefficient
$\Im$—operator that extracts the imaginary part of a complex number Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

[1] E. Setter and I. Bucher, "Flexural vibration patterning using an array of actuators," *Journal of Sound and Vibration*, vol. 330, pp. 1121-1140, 2011.

[2] R. Gabai and I. Bucher, "Excitation and sensing of multiple vibrating traveling waves in one-dimensional structures," *Journal of Sound and Vibration*, vol. 319, pp. 406-425, 2009.

[3] S. Ueha and Y. Tomikawa, "Ultrasonic Motors: Theory and Applications, with contributions from M. Kurosawa and N. Nakamura," Oxford, Clarendon Press, 1993.

[4] M. Jean-François, B. Stéphane, and B. François, "On the generation and identification of traveling waves in non-circular structures—application to innovative piezoelectric motors," *Smart Materials and Structures*, vol. 7, p. 337, 1998.

[5] A. Minikes and I. Bucher, "Noncontacting lateral transportation using gas squeeze film generated by flexural traveling waves—Numerical analysis," *Journal of the Acoustical Society of America*, vol. 113, pp. 2464-2473, May 2003.

[6] A. Minikes, I. Bucher, and S. Haber, "Levitation force induced by pressure radiation in gas squeeze films," *Journal of the Acoustical Society of America*, vol. 116, pp. 217-226, July 2004.

[7] C. Li, W. Yuechao, M. Shugen, and L. Bin, "Analysis of traveling wave locomotion of snake robot," in *Robotics, Intelligent Systems and Signal Processing, 2003. Proceedings. 2003 IEEE International Conference on*, 2003, pp. 365-369 vol. 1.

[8] P. Kerrebrock, "Traveling wave generator" US 2003/0029257 A1, Sep. 16, 2003.

[9] B. Chan, N. J. Balmforth, and A. E. Hosoi, "Building a better snail: Lubrication and adhesive locomotion," *Physics of Fluids*, vol. 17, November 2005.

[10] J. G. Brian Chan, Anette Hosoi, "Mechanical crawler" US 2007/0079997 A1, Nov. 17, 2009.

[11] C. A. Clark, "UNDULATING SURFACE DRIVING SYSTEM," U.S. Pat. No. 3,221,702, Dec. 7, 1965.

[12] C. P. Gusler, "Methods for using a linear propulsor with linear motion" US 2006/0172625 A1, Jul. 17, 2007.

[13] C. B. Momsen, "HYDRODYNAMIC TRAVELLING WAVE PROPULSION APPARATUS," U.S. Pat. No. 3,154,043, Oct. 27, 1964.

[14] F. Akistowicz, "VEHICLE PROPULSION APPARATUS," U.S. Pat. No. 3,066,637, Dec. 4, 1962.

[15] A. O. Nunda, "UNDULATING BODY PROPULSION SYSTEM," U.S. Pat. No. 3,623,566, Nov. 30, 1971.

[16] J. H. Saringer, "Mechanism for generating wave motion" U.S. Pat. No. 6,029,294, Feb. 29, 2000.

[17] K. Abe, "Wave motion simulator" U.S. Pat. No. 3,964,316, Jun. 22, 1976.

[18] S. Childress, "Mechanics of Swimming and Flying," Cambridge University Press, 1981.

[19] N. Cohen and J. H. Boyle, "Swimming at low Reynolds number: a beginners guide to undulatory locomotion," *Contemporary Physics*, vol. 51, pp. 103-123, Mar. 1, 2010 2010.

[20] C. Brennen and H. Winet, "Fluid Mechanics of Propulsion by Cilia and Flagella," *Annual Review of Fluid Mechanics*, vol. 9, pp. 339-398, 1977.

[21] J. J. Abbott, K. E. Peyer, M. C. Lagomarsino, L. Zhang, L. Dong, I. K. Kaliakatsos, and B. J. Nelson, "How Should Microrobots Swim?," *The International Journal of Robotics Research*, vol. 28, pp. 1434-1447, November/December 2009 2009.

[22] A. H. Meng, N.-T. Nguyen, and R. M. White, "Focused Flow Micropump Using Ultrasonic Flexural Plate Waves," *Biomedical Microdevices*, vol. 2, pp. 169-174, 2000.

[23] K. Nakahara, K. Yoshimura, Y. Okayama, and N. Miki, "A peristaltic micropump using traveling waves of polymer membranes driven by a single actuator," in *Micro Electro Mechanical Systems (MEMS), 2011 IEEE 24th International Conference on*, 2011, pp. 1083-1086.

[24] C. HERNANDEZ, Y. BERNARD, and A. RAZEK, "ULTRASONIC TRAVELING WAVE MICROPUMP FOR LIQUID," WO/2011/154634, Dec. 15, 2011.

[25] S. A.-S. David Elata, "Motion imparting device" US 2008/0193307 A1, Jun. 24, 2004.

[26] B. J. Nelson, I. K. Kaliakatsos, and J. J. Abbott, "Microrobots for Minimally Invasive Medicine," *Annual Review of Biomedical Engineering*, vol. 12, pp. 55-85, Jul. 1, 2010 2010.

[27] M. P. Norton, "Fundamentals of Noise and Vibration Analysis for Engineers" Cambridge University Press, 1989.

[28] E. Lauga and T. R. Powers, "The hydrodynamics of swimming microorganisms," *Reports on Progress in Physics*, vol. 72, September 2009.

[29] H. A. Rothbart, "Cam design handbook," McGraw-Hill, 2004.

[30] S. Timoshenko and S. Woinowsky-Krieger, "Theory of Plates and Shells (Engineering Societies Monographs)" McGraw-Hill, 1959.

[31] E. Setter, I. Bucher, and S. Haber, "Low Reynolds number swimmer utilizing surface traveling waves—analytical and experimental study," Submitted to *Phys. Rev. E*.

What is claimed is:

1. A system for generating a mechanical wave having a wavelength $\lambda$, the system comprising:
   an elastic tubular shell, having an axis;
   a camshaft positioned within said tubular shell, said camshaft having plurality of rotatable cams, serially mounted on a shaft along said axis to form a varying phase angle along said shaft; and
   a plurality of cam followers arranged circumferentially about each cam, such that a rotary motion of said cams generates a linear motion of said cam followers to radially bias an internal wall of said shell;
   wherein said variation of said phase angle is from about $2\pi(L/\lambda)/(N \cdot Nc)-X$ to about $2\pi(L/\lambda)/(N \cdot Nc)+X$, wherein N is a number of angular wavelengths along a periphery of each cam, $N_c$ is a number of said cams, L is a distance between a first cam and a last cam of said camshaft, and X is less than $10°/N$.

2. The system of claim 1, further comprising a plurality of arcs respectively mounted on said plurality of cam followers, such that said arcs engage said internal wall during at least part of said linear motion.

3. The system of claim 1, wherein a number and separation of said cams along said shaft is selected such that $kL/\lambda$ is generally an integer, where k is an integer.

4. The system of claim 1, wherein said number and said separation of said cams along said shaft is selected such that $kL/(\lambda N_c)$ is non-integer, where k is an integer.

5. The system of claim 1, wherein said plurality of cam followers comprises three cam followers per cam.

6. The system of claim 1, further comprising a motor operatively connected to said shaft and communication device for remote activation, control and deactivation of said motor.

7. The system of claim 1, wherein at least one of said cams has a single-harmonic profile.

8. The system of claim 1, wherein at least one of said cams has a multi-harmonic profile.

9. The system of claim 1, wherein said variation of said phase angle is selected to generate a three-dimensional traveling wave along said shell.

10. An autonomous self-propelled vehicle, comprising the system of claim 1.

11. The vehicle of claim 10, adapted for being introduced into a body lumen of a mammal.

12. The vehicle of claim 11, wherein said body lumen selected from the group consisting of a vein, an artery, a gastrointestinal tract and a colon.

13. The vehicle of claim 10, adapted for being introduced into a structure selected from the group consisting of a pipe, a channel, a building duct, a borehole and a pool.

14. A self-propelled endoscope system, comprising the system of claim 1.

15. A pump, comprising the system of claim 1.

16. A method of displacing an object, comprising introducing a self-propelled vehicle having the object into a fluid medium to generate therein a mechanical wave having a wavelength $\lambda$, wherein said self-propelled vehicle comprises:
   an elastic tubular shell, having an axis;
   a camshaft positioned within said tubular shell, said camshaft having plurality of rotatable cams, serially mounted on a shaft along said axis to form a varying phase angle along said shaft; and
   a plurality of cam followers arranged circumferentially about each cam, such that a rotary motion of said cams generate a linear motion of said cam followers to radially bias an internal wall of said shell;
   wherein said variation of said phase angle is from about $2\pi(L/\lambda)/(N \cdot Nc)-X$ to about $2\pi(L/\lambda)/(N \cdot Nc)+X$, wherein N is a number of angular wavelengths along a periphery of each cam, $N_c$ is a number of said cams, L is a distance between a first cam and a last cam of said camshaft, and X is less than $10°/N$.

17. The method of claim 16, wherein said fluid medium is characterized by a Reynolds number less than 1.

18. The method of claim 16, wherein said fluid medium is in a body lumen of a mammal.

19. The method of claim 18, wherein said body lumen selected from the group consisting of a vein, an artery, a gastrointestinal tract and a colon.

20. The method of claim 16, wherein said fluid medium is contained in a structure selected from the group consisting of a pipe, a channel, a building duct, a borehole and a pool.

21. The method of claim 16, wherein said object is at least one of: a drug, a camera, a distal end of an endoscope, a sensor, a communication device, a stent, an electrical stimulation device, and a magnetic stimulation device.

22. A method of pumping, comprising fixating a pump in a lumen having a fluid medium therein and activating said pump to generate in the fluid medium a mechanical wave having a wavelength $\lambda$, wherein said pump comprises:
   an elastic tubular shell, having an axis;
   a camshaft positioned within said tubular shell, said camshaft having plurality of rotatable cams, serially mounted on a shaft along said axis to form a varying phase angle along said shaft; and
   a plurality of cam followers arranged circumferentially about each cam, such that a rotary motion of said cams generate a linear motion of said cam followers to radially bias an internal wall of said shell;
   wherein said variation of said phase angle is from about $2\pi(L/\lambda)/(N \cdot Nc)-X$ to about $2\pi(L/\lambda)/(N \cdot Nc)+X$, wherein N is a number of angular wavelengths along a periphery of each cam, $N_c$ is a number of said cams, L is a distance between a first cam and a last cam of said camshaft, and X is less than $10°/N$.

23. The method of claim 22, wherein said fluid medium is body liquid.

24. The method of claim 22, wherein a smallest dimension of said shell is at least 1 centimeter, and wherein the fluid medium is liquid having a viscosity of at least 10000 cSt.

25. The method of claim 22, wherein a smallest dimension of said shell is from about 1 mm to about 1 centimeter, and wherein the fluid medium is liquid having a viscosity of at least 1 cSt.

26. The method of claim 22, wherein said fluid medium is a biological fluid.

* * * * *